(12) United States Patent
van den Bogert

(10) Patent No.: US 7,549,969 B2
(45) Date of Patent: Jun. 23, 2009

(54) APPARATUS FOR ASSISTING BODY MOVEMENT

(75) Inventor: Antonie J. van den Bogert, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 645 days.

(21) Appl. No.: 10/938,262

(22) Filed: Sep. 10, 2004

(65) Prior Publication Data
US 2005/0059908 A1 Mar. 17, 2005

Related U.S. Application Data

(60) Provisional application No. 60/502,006, filed on Sep. 11, 2003.

(51) Int. Cl.
*A61F 13/00* (2006.01)
(52) U.S. Cl. .............................. 602/16; 602/23; 602/26; 602/27
(58) Field of Classification Search ...................... 602/5, 602/19, 16, 20, 23, 26, 27; 482/51; 428/4, 428/75; 135/67
See application file for complete search history.

(56) References Cited

U.S. PATENT DOCUMENTS

| | | | |
|---|---|---|---|
| 2,010,482 A | 8/1935 | Cobb | |
| 5,621,985 A | 4/1997 | Frost | |
| 5,658,242 A | 8/1997 | McKay et al. | |
| 5,662,693 A | 9/1997 | Johnson et al. | |
| 5,899,869 A | 5/1999 | Barrack, Jr. et al. | |
| 5,961,476 A | 10/1999 | Betto et al. | |
| 6,689,074 B2 | 2/2004 | Seto et al. | |
| 2002/0094919 A1 | 7/2002 | Rennex et al. | |
| 2003/0144620 A1 | 7/2003 | Sieller et al. | |

FOREIGN PATENT DOCUMENTS

GB  2 278 041 A  11/1994

OTHER PUBLICATIONS

"Berkelely Robotics Laboratory", Website: http://bleex.me.Berkeley.edu/bleex.htm, dated 2003.

(Continued)

*Primary Examiner*—Kim M Lewis
(74) *Attorney, Agent, or Firm*—Tarolli, Sundheim, Covell & Tummino LLP

(57) ABSTRACT

An apparatus for assisting in body movement includes a framework which is connectable with a human body and an elastic force transmission system connected with the framework. The elastic force transmission system stores energy during a first portion of movement of the human body and releases the stored energy during a second portion of the movement of the human body. The elastic force transmission system includes an elongated force transmission component which is resiliently extendable under the influence of force transmitted through the framework. Although the apparatus can be used in association with any desired portion of the human body, it may be particularly advantageous to use the apparatus in association with one or both legs of the human body.

62 Claims, 5 Drawing Sheets

OTHER PUBLICATIONS

"Robot Suit HAL (Hybrid Assitive Limb)", Website: http://www.cyberdyne.jp/ENG/hal.html, dated 2004.

"Book 4—Center for Orthotics Design Catalog", Website: www.centerfororthoticsdesign.com, dated Jun. 2001.

An Abstract of Research Disclosure No. XP-002322376, undated.

Research Disclosure No. XP-002322421, dated Oct. 14, 2003 for "Exotendons for Assistance of Human Locomotion".

Research Disclosure No. XP-002322422, dated Sep. 2000 for "Exoskeleton for Soldier Enhancement Systems Feasilbility Study".

* cited by examiner

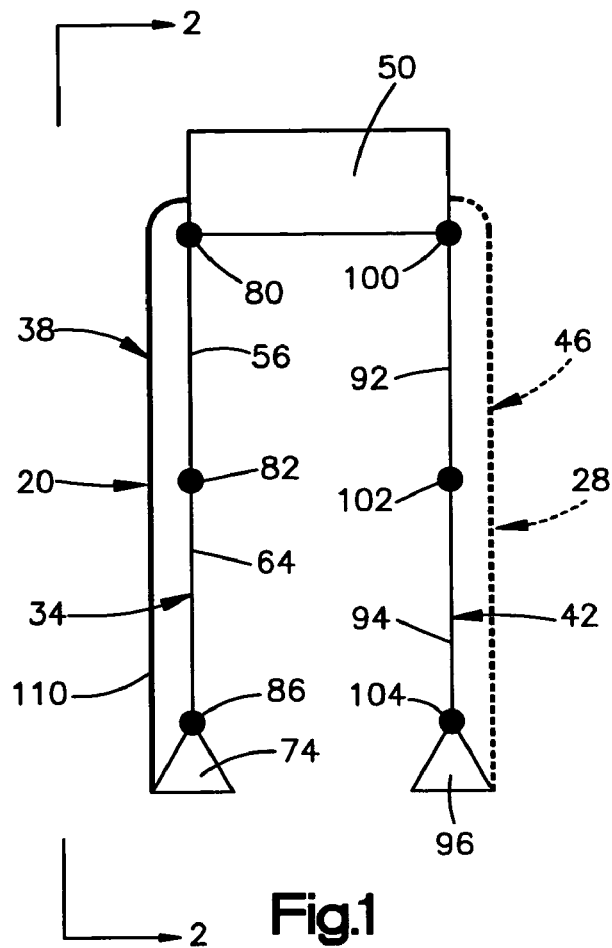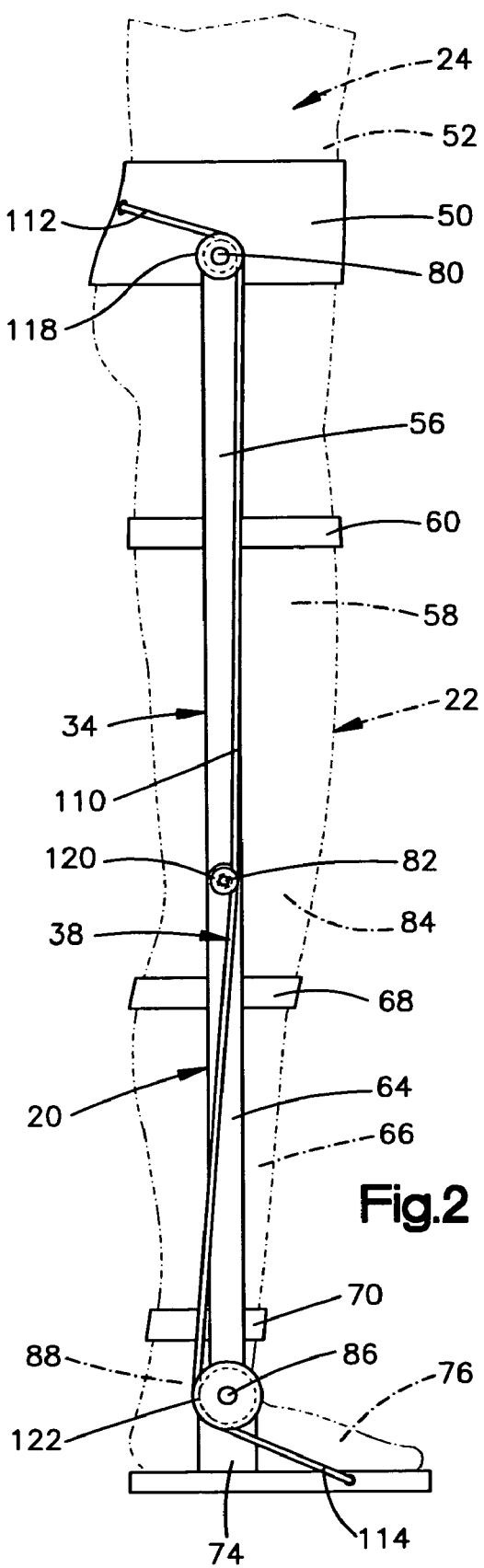

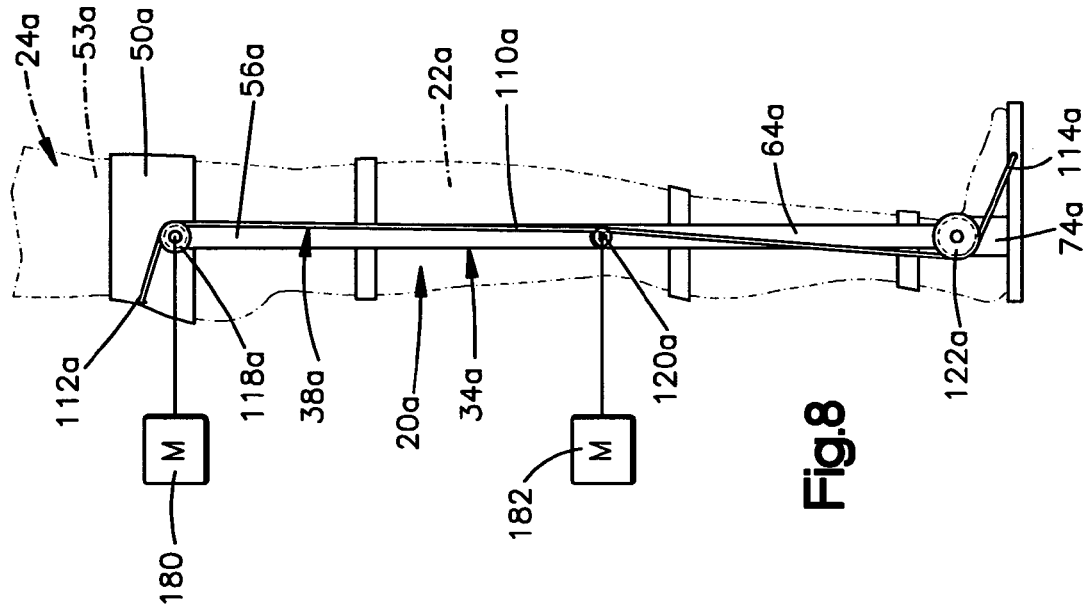
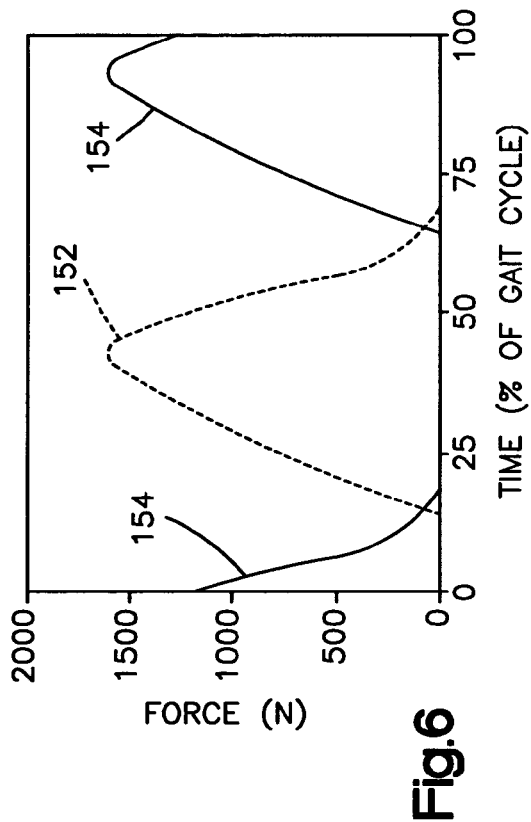
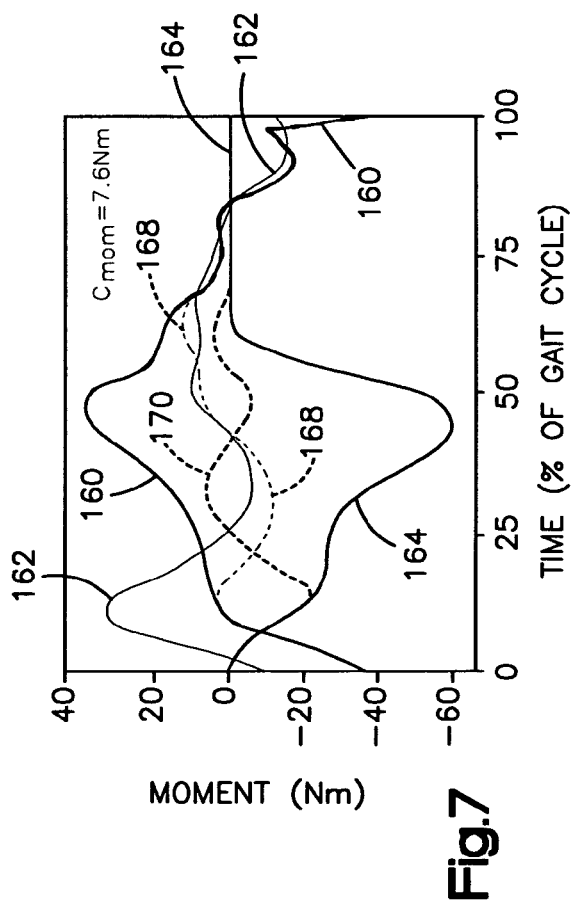

APPARATUS FOR ASSISTING BODY MOVEMENT

RELATED APPLICATIONS

This application claims the benefit of the earlier filing date of Provisional Patent Application Ser. No. 60/502,006, filed Sep. 11, 2003 by Antonie J. van den Bogert and entitled "Exotendons for assistance of human locomotion" (Confirmation No. 4670). The disclosure in the aforementioned provisional application Ser. No. 60/502,006 is hereby incorporated herein in its entirety by this reference thereto.

BACKGROUND OF THE INVENTION

Powered robotic frameworks or exoskeletons are currently under development for enhancement of human locomotor performance in the military, in industry and for patients with mobility impairments. When compared to wheeled vehicles and wheelchairs, exoskeleton-based assistive devices have several advantages. They allow the user to go outside of paved surfaces, and there is the possibility of an intuitive haptic user interface, which senses the user's intended movement and assists it automatically.

Energy efficiency is, however, a major problem for such technology. Wheeled vehicles, once at constant speed, only require power to overcome small amounts of energy lost due to rolling friction and air resistance. Legged systems, on the other hand, require considerable additional energy to accelerate and decelerate the limbs and to dynamically support the body mass against gravity. Inverse dynamic analysis of human movement has shown that, when driven by hypothetical motors at each joint, walking would require about 60 W of steady state power. Powered exoskeletons for military applications are estimated to require 600 W of steady state power at running speeds when carrying a maximum payload.

Supplying power to such devices for several hours is well beyond the capabilities of current battery technology. Only an internal combustion engine can provide sufficient energy while still being small enough to be carried, with sufficient fuel, in a backpack. However, even when an internal combustion engine is utilized, the backpack tends to be heavy and cumbersome.

Efficient legged locomotion systems can be found in nature. Large terrestrial animals typically do not power their movements with a motor at each joint. Muscles often span multiple joints, which results in energy-saving power transfers when a movement simultaneously requires negative power at one joint and positive power at another joint. Furthermore, it is often possible to make effective use of passive elastic properties to generate part of the required force or power without metabolic cost, especially when muscle-tendon units span multiple joints.

These naturally occurring mechanisms are highly developed in horses. Of the seven musculotendinous structures in the distal part of the equine hindlimb, four have become almost completely tendinous and the others have short muscle fibers with strong parallel elastic tissue and a long series elastic component spanning up to four major joints. Measurements of bone kinematics and tendon strain have shown that forces in the digital flexors and in the Peroneus Tertius are consistent with passive elastic mechanisms for force generation. This limb design results in various "pogo-stick" and "catapult" mechanisms that contribute to efficient locomotion. Consequently, horses consume 50% less metabolic energy for running than humans, per kg of body weight.

In contrast to these efficient natural systems, current designs for powered exoskeletons use a traditional robotics approach where movement is generated by stiff servomotors, each moving a single joint. This approach is thought to be responsible for poor efficiency and stiff-legged gait in legged robots.

SUMMARY OF THE INVENTION

An apparatus for use in assisting human body movement includes a framework which is connectable with the human body and an elastic force transmission system which is connected with the framework. The elastic force transmission system stores energy during a first portion of movement of human body and releases the stored energy during a second portion of the movement of the human body. The elastic force transmission system may include an elongated force transmission component which is resiliently extendable to store energy. The elongated force transmission component may be resiliently contractible to release the stored energy. The elongated force transmission component may span one or more joints in the human body.

The framework may include a plurality of frame members which are interconnected by a plurality of frame joints which are disposed adjacent to joints in the human body. A plurality of rotatable members may be connected with the framework and disposed adjacent to the frame joints. The elongated force transmission component may be connected with the framework and may engage arcuate surfaces on the rotatable members.

The elongated force transmission component may be offset in an anterior direction where the elongated force transmission component engages arcuate surfaces on one or more rotatable members. The elongated force transmission component may be offset in a posterior direction at a location where the force transmission component engages one or more additional rotatable members. A first rotatable member may have a radius which is greater than the radius of a second rotatable member and less than the radius of a third rotatable member. Of course, a greater or lesser number of rotatable members having radii with any desired size relationship may be used.

Although the apparatus may be utilized with many different portions of a human body, such as an arm, the apparatus may advantageously be used in association with a leg. When this is the case, a first rotatable member may be adjacent to a hip joint in the human body. A second rotatable member may be adjacent to a knee joint in the leg of the human body. A third rotatable member may be disposed adjacent to an ankle joint in the leg of the human body. It is believed that the arcuate surfaces on the rotatable members may be sized such that the product of the radii of the first and third arcuate surfaces times the stiffness of the force transmission system is equal to between 51 and 95 Newton meters. However, different embodiments of the invention may utilize different numbers of rotatable members and have a different relationship between rotatable member size and force transmission system stiffness.

The present invention includes many different features which may be utilized either separately or in various combinations with each other. For example, the rotatable members may be sized and located in different ways. The elongated force transmission component may have any one of many different constructions. The apparatus may be used with only one leg and/or arm. Alternatively, the apparatus may be used with both legs and/or arms. It should be understood that features of the invention may be used in ways or in combinations other than the foregoing examples.

BRIEF DESCRIPTION OF THE DRAWINGS

The foregoing and other features of the present invention will become more apparent upon a consideration of the following description taken in connection with the accompanying drawings wherein:

FIG. 1 is a highly schematized front elevational view of an apparatus constructed in accordance with the present invention;

FIG. 2 is a schematic side elevational view, taken generally along the line 2-2 of FIG. 1, further illustrating how apparatus constructed in accordance with the present invention is connected with a leg of a human body;

FIG. 6 is a graph illustrating the manner in which force varies in elongated force transmission components of the apparatus of FIGS. 1-5 during a walking gait cycle;

FIG. 7 is a graphic illustrating the manner in which moment varies in hip, knee, and ankle joints of a human body during walking with and without the apparatus of the present invention;

FIG. 8 is a schematic illustration, similar to FIG. 2, depicting the manner in which motors may be connected with the apparatus of FIG. 2 to further assist in movement of a leg in a human body;

DESCRIPTION OF SPECIFIC PREFERRED EMBODIMENTS OF THE INVENTION

General Description

Figure 4:
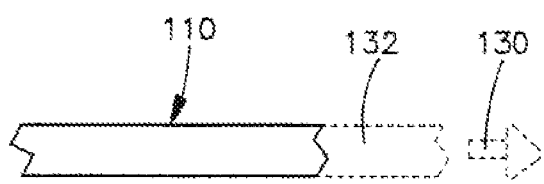
FIG. 4 is a schematic illustration of one embodiment of an elongated force transmission component which is utilized in the apparatus of FIG. 3.

An apparatus 20 (FIG. 1) constructed in accordance with the present invention is utilized to assist in movement of a right leg 22 (FIG. 2) in a human body 24. An apparatus 28 (FIG. 1) constructed in accordance with the present invention is utilized to assist in movement of a left leg 30 (FIG. 3) in the human body 24. The apparatus 20 and 28 have the same general construction and may be used separately or together. Thus, only the apparatus 20 may be used with the right leg 22. Similarly, only the apparatus 28 may be used with the left leg 30. However, it is believed that the apparatus 20 and 28 may advantageously be used with both legs in the manner illustrated schematically in FIGS. 1-3. It should be understood that apparatus constructed in accordance with the present invention may be used with portions of the human body other than the legs 22 and/or 30.

Figure 3:
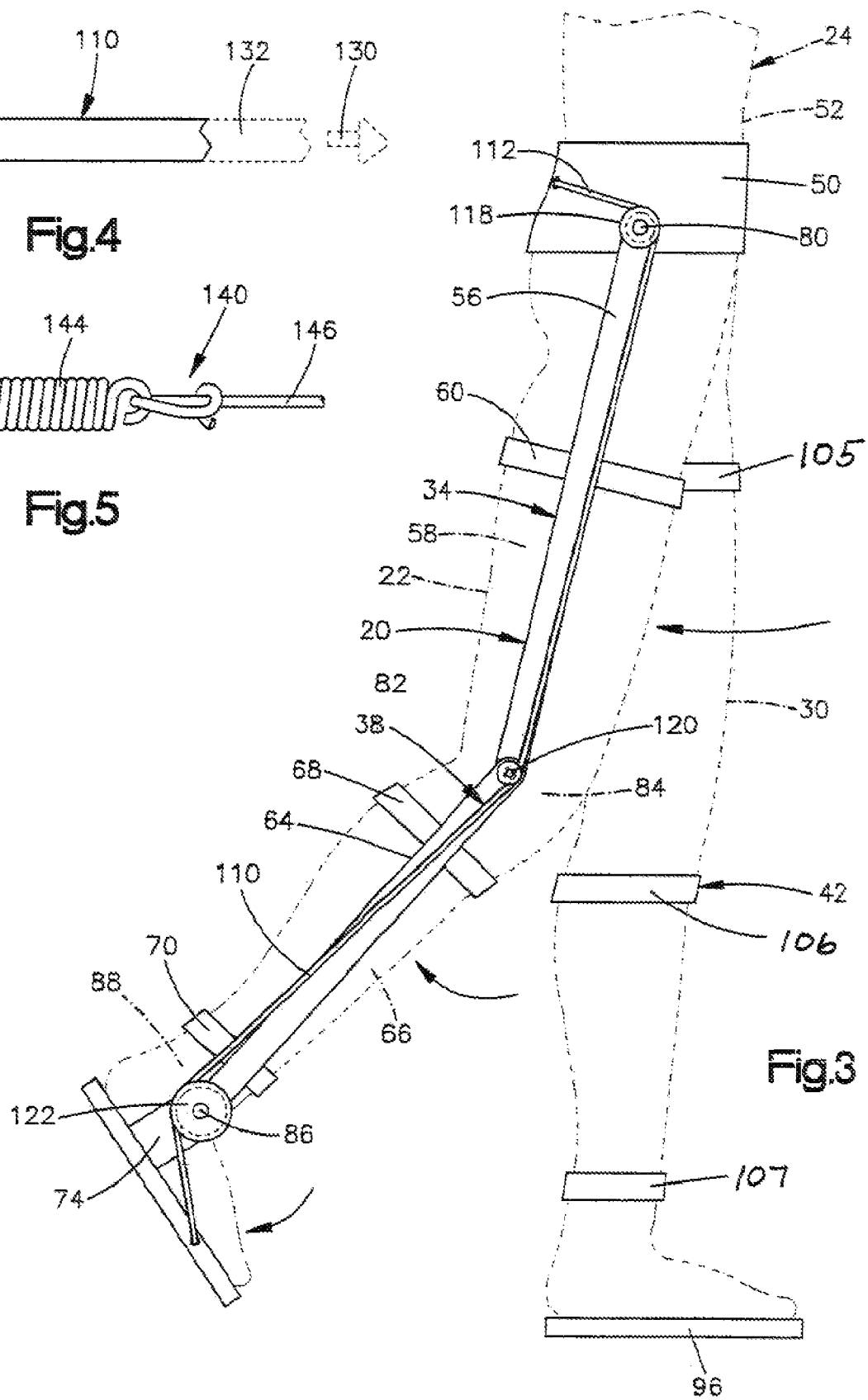
FIG. 3 is a schematic illustration depicting the manner in which a leg of a human body moves during walking.

The apparatus 20 includes a right framework or exoskeleton 34 (FIG. 1) which extends along the right leg 22 (FIG. 2) of the human body 24. A right elastic force transmission system 38 is connected with the right framework 34 and extends along the right leg 22 (FIGS. 1-3). Similarly, the apparatus 28 includes a left framework or exoskeleton 42 (FIG. 1) which extends along the left leg 30 (FIG. 3) of the human body 24. A left elastic force transmission system 46 (FIG. 1) is connected with the left framework 42 and extends along the left leg 30.

The right elastic force transmission system 38 (FIGS. 1 and 2) is connected with the right framework 34 and stores energy during a first portion of walking movement of the right leg 22. The right elastic force transmission system 38 releases stored energy to assist movement of the right leg 22 during a second portion of the walking movement of the right leg. Similarly, the left elastic force transmission system 46 (FIG. 1) is connected with the left framework 42 and stores energy during a first portion of walking movement of the left leg 30 (FIGS. 1 and 3). The left elastic force transmission system 46 releases stored energy to assist movement of the left leg 30 during a second portion of the walking movement of the left leg.

Framework

The right framework 34 (FIG. 2) is effective to transmit force between the human body 24 and the right elastic force transmission system 38. The right framework 34 includes a pelvic frame member 50 which extends around a pelvic portion 52 of the human body 24. The pelvic frame member 50 is formed by a plurality of rigid metal (aluminum) and/or polymeric sections which are hingedly interconnected. When the frame member 50 is in the closed condition of FIG. 2, it encircles a pelvic portion 52 of the body 24. Releasable connectors are provided to enable the frame member 50 to be opened and removed from the pelvic portion 52 of the body 24.

An upper frame member 56 extends downward from the pelvic frame member 50 along a femoral portion 58 of the right leg 22. The rigid upper frame member 56 is connected with the femoral portion 58 of the right leg 22 by a strap or band 60. Of course, the upper frame member 56 may be connected with the femoral portion 58 of the leg 22 by a device other than the strap 60.

A lower frame member 64 extends downward from the upper frame member 56. The rigid lower frame member 64 is connected with a tibial portion 66 of the right leg 22 by straps 68 and 70. Of course, the lower frame member 64 may be connected with the tibial portion of the leg 22 by a device other than the straps 68 and 70.

A rigid foot frame member 74 is connected with a foot portion 76 of the human body 24. The foot frame member 74 may extend along both sides and beneath the foot portion 76. The frame members 56, 64, and 74 may be formed of a light weight metal, such as aluminum, and/or a suitable polymeric material. The frame members 56, 64, and 74 may be configured and/or padded minimize wearer discomfort.

In addition to the frame members 50, 56, 64 and 74, the right framework 34 includes frame joints which pivotally interconnect the frame members. Thus, a hip frame joint 80 (FIGS. 1-3) connects the pelvic frame member 50 with the upper frame member 56. The hip frame joint 80 allows the upper frame member 56 to pivot about an axis which is disposed in general alignment with pivot axis of the right hip joint in the human body 24. The pivot axis for the hip frame joint 80 is generally parallel to or is disposed in a coronal plane dividing the body into equal front and back parts. The pivot axis for the hip frame joint 80 is generally perpendicular to a median plane which divides the body 24 into equal right and left halves.

Similarly a knee frame joint 82 pivotally connects the upper frame member 56 with the lower frame member 64. The knee frame joint is disposed adjacent to a knee 84 (FIG. 2) in the right leg 22. The axis about which the upper frame member 56 and lower frame member 64 pivot relative to each other at the knee frame joint 82 is disposed in general alignment with a pivot axis for the knee 84. The pivot axis for the knee frame joint 82 extends generally parallel to the pivot axis for the hip frame joint 80.

The lower frame member 64 is pivotally connected with the foot frame member 74 by an ankle frame joint 86. The ankle frame joint 86 has a pivot axis which is disposed in general alignment with a pivot axis for an ankle portion 88 (FIGS. 2 and 3) of the right leg 22. The pivot axis for the ankle frame joint 86 extends generally parallel to the pivot axis for the hip frame joint 80.

The frame joints 80, 82 and 86 provide the right framework 34 with an articulated construction which enables the femur and tibia to be moved in both extension and flexion. In addition, the right foot 76 can be moved in both dorsiflexion and planterflexion.

It should be understood that the framework 34 has been illustrated schematically in FIG. 2. The framework 34 may have any one of many known constructions. For example, the framework may have a construction similar to the construction of a reciprocating gait orthosis which is commercially available from Center For Orthotics Design, Inc., A Fillauer Company, having a place of business at 561 Division Street, Campbell, Calif. 95008. Of course, the framework 34 may have any one of many other known constructions. For example, the framework may have a construction which is similar to the constructions disclosed in U.S. Pat. Nos. 4,697,808; 5,054,476; 5,662,693; and/or 5,961,476.

Although only the right framework 34 is illustrated in FIG. 2, it should be understood that the left framework 42 (FIG. 1) has a construction which is symmetrical to the construction of the right framework 34. Of course, the left framework 42 is modified for use in association with the left leg 30 of a human body 24 rather than the right leg 22. Therefore, the left framework 42 is a mirror image of the right framework 34.

The left framework 42 (FIG. 1) includes a rigid upper frame member 92 which is pivotally connected with the pelvic frame member 50. The pelvic frame member 50 forms part of both the right framework 34 and the left framework 42. The left framework 42 also includes a rigid lower frame member 94 which is pivotally connected with the upper frame member 92. A foot frame member 96 pivotally is connected with the lower frame member 94.

In addition, the left framework 42 includes a hip frame joint 100 which pivotally interconnects the pelvic frame member 50 and the upper frame member 92. The hip frame joint 100 has a pivot axis which is disposed in general alignment with a pivot axis of the left hip of the human body 24. The pivot axis of the left hip frame joint 100 is substantially coincident with the pivot axis of the left and right hips and the pivot axis of the right hip frame joint 80.

A knee frame joint 102 (FIG. 1) pivotally connects the upper frame member 92 with the lower frame member 94. The knee frame joint 102 has a pivot axis which is disposed in general alignment with the pivot axis of the left knee in the human body 24. The pivot axis of the left knee frame joint 102 is substantially coincident with the pivot axes of the left and right knees and the pivot axis of the right knee frame joint 82 when the right and left legs 22 and 30 are in a side-by-side relationship. The pivot axis of the left knee frame joint 102 is generally parallel to the pivot axis of the left hip frame joint 100.

An ankle frame joint 104 (FIG. 1) pivotally connects the lower frame member 94 to the foot frame member 96. The ankle frame joint 104 has a pivot axis which is disposed in general alignment with the pivot axis of the left ankle in the human body 24. The pivot axis of the left ankle frame joint 104 is substantially coincident with the pivot axis of the left and right ankles and the pivot axis of the right ankle frame joint 86 when the left and right legs 22 and 30 are in a side-by-side relationship. The pivot axis of the left ankle frame joint 104 is generally parallel to the pivot axis of the left hip frame joint 100.

The left framework 42 is connected with the left leg of the human body 24 by straps 108, 110, and 112 (FIG. 3). It is contemplated that one or more of the straps 108, 110 and 112 may be omitted. For example, the strap 108 may be omitted. Of course, one or more the right straps 60, 68 and 70 may also be omitted.

The right framework 34 and left framework 42 are both connected to the frame member 50 which extends around the pelvic or waist portion 52 of the human body 24. Therefore, the pelvic frame member 50 may be considered as forming a portion of both the right framework 34 and the left framework 42. Alternatively, the left framework 42 and right framework 34 may be considered as being a single framework having two leg portions which are connected by the pelvic frame member 50. It should be understood that the right and left frameworks 34 and 42 may be used together or may be used separately.

The foregoing description of the frameworks 34 and 42 has been in association with the legs 22 and 30 of the human body 24. If desired, the frameworks may be utilized in association with a different portion of the human body 24. For example the frameworks may be used in association with the arms of a human body.

Elastic Force

Transmission System

The right elastic force transmission system 38 includes a right elongated force transmission component 110 (FIGS. 1 and 2). The elongated force transmission component 110 may be referred to as an exotendon. An upper end portion 112 of the elongated force transmission component 110 is fixedly connected to the frame member 50 which extends around the pelvic or waist portion 52 of the human body 24. The opposite or lower end portion of the right elongated force transmission component 110 is fixedly connected to the foot frame member 74 at a location adjacent to the ball of the foot portion 76, that is, adjacent to the location where head end portions of the metatarsals engage the phlanges in the foot portion 76. This results in the spanning of the hip, knee and ankle joints with the elastic force transmission component 110. However, the elastic force transmission component may span a greater or lesser number of joints if desired.

In addition to the elongated force transmission component 110, the right elastic force transmission system 38 includes a plurality of rotatable members. The rotatable members are effective to deflect the elongated force transmission component 110 so that it is offset from axes of rotation of at least some of the frame joints 80, 82 and 86. Although the rotatable members may have any desired construction, they may be pulleys.

An upper rotatable member 118 (FIG. 2) is rotatable about an axis which is coincident with the pivot axis of the hip frame joint 80 and is disposed in general alignment with a pivot axis of a right hip joint in the human body 24. Similarly, a rotatable member 120 is disposed adjacent to the knee 84. The rotatable member 120 is rotatable about an axis which is coincident with a pivot axis of the knee frame joint 82 and is disposed in general alignment with a pivot axis of the knee 84. In addition, a lower rotatable member 122 is rotatable about an axis which is coincident with a pivot axis of the ankle frame joint 86 and is disposed in general alignment with a pivot axis of the ankle 88.

The upper rotatable member 118 (FIG. 2) is effective to offset a portion of the right elongated force transmission component 110 which engages the upper rotatable member, in an anterior direction relative to the axis of rotation of the rotatable member and the pivot axis of the upper frame joint 80. Similarly, the rotatable member 120 is effective to offset a portion of the right elongated force transmission component 110 which engages the rotatable member 120, in the anterior direction relative to the axis of rotation of the rotatable member and the pivot axis of the knee frame joint 82. The lower rotatable member 122 is effective to offset a portion of the right elongated force transmission component 110 which engages the rotatable member 122, in the posterior direction relative to the axis of rotation of the rotatable member and the pivot axis of the ankle frame joint 86.

The upper rotatable member 118 (FIG. 2) has an arcuate outer side surface which is engaged by the right elongated force transmission component 110. The arcuate outer side surface of the upper rotatable member 118 has a first radius of curvature. The rotatable member 120 has an arcuate side surface which engages the right elongated force transmission component 110. The arcuate side surface of the rotatable member 120 has a radius of curvature which is smaller than the radius of curvature of the arcuate surface on the upper rotatable member 118. The lower rotatable member 122 has an arcuate side surface which engages the right elongated force transmission component 110. The arcuate side surface of the lower rotatable member 122 has a radius of curvature which is larger than the radius of curvature of the upper rotatable member 118.

The rotatable members 118, 120, and 122 may have many different constructions. In the illustrated embodiment of the invention (FIGS. 2 and 3), the rotatable members 118, 120 and 122 are pulleys. Each of these pulleys have a circular configuration with an annular groove or rim which forms an arcuate side surface and engages the right elongated force transmission component 110. However, the rotatable members 118, 120, and 122 may have a different construction if desired. For example, the rotatable members 118, 120 and 122 may be formed with arcuate side surfaces which have an extent which is less than 360°. Alternatively, the rotatable members 118, 120, and 122 may be formed as cylindrical bodies which are rotatable about spindles.

If desired, the right elastic force transmission system 38 may be constructed in such a manner as to have each of the members 118, 120 and 122 fixed relative to one of the frame members 50, 56, 64, or 74. However, this would result in sliding movement of the elongated force transmission component 110 relative to the members 118, 120, and 122 during flexion and extension of the right leg 22. By having the members 118, 120, and 122 rotatable relative to the framework 34, any tendency for the elongated force transmission component 110 to slide relative to the members is minimized or eliminated.

The performance of the apparatus 20 may be varied by varying the radii of the arcuate side surfaces on the rotatable members 118, 120, and 122 which engage the force transmission component 110. In addition, the performance of the apparatus 20 may be varied by varying the stiffness, that is, the spring force constant, of the elastic force transmission system 38.

It is believed that the circular arcuate side surface disposed on the rotatable member 118 and engaged by the elongated force transmission component 110 should have a radius which is greater than the radius of the circular arcuate side surface disposed on the rotatable member 120 and engaged by the elongated force transmission component 110. It is also believed that the circular arcuate side surface disposed on the rotatable member 118 and engaged by the elastic force transmission component 110 should have a radius which is less than a radius of the circular arcuate surface disposed on the lower rotatable member 122 and engaged by the elastic force transmission component 110. However, it should be understood that the apparatus 20 may be constructed with a different relationship between the radii on the rotatable members 118, 120, and 122 if the performance of the apparatus 20 is acceptable.

It is believed that the performance of the apparatus 20 may be made very satisfactory by having the product of the radius of curvature for the arcuate side surface disposed on the rotatable member 118 ($r_1$), the radius of curvature for the arcuate surface on the rotatable member 122 ($r_3$), and the stiffness of the elastic force transmission system 38 (k) equal to between fifty-one (51) and ninety-five (95) Newton meters. This may be expressed by an equation of: $(r_1) \cdot (r_3) \cdot (k) = 51$ to 95 Newton meters. It is believed that the efficiency of the apparatus 20 is optimized when the product of the radius of curvature of the arcuate surface on the rotatable member 118 ($r_1$) and the radius of curvature of the arcuate surface on the lower rotatable member 122 ($r_3$) and the stiffness or spring force constant of the elastic force transmission system 38 (k) is equal to approximately 73 Newton meters. Although the optimal relationship between the product of $(r_1) \cdot (r_3) \cdot (k)$ is approximately 73 Newton meters, it should be understood that the apparatus 20 is still functionally satisfactory and provides significant advantages when the product is somewhat greater than or less than seventy-three Newton meters.

In one specific embodiment of the invention, the elastic force transmission system 38 includes an elongated force transmission component 110 formed by a band (FIG. 4) of resilient polymeric material. The resilient elastomeric material forming the band of the force transmission component 110 is integrally formed as one piece and extends from the upper end portion 112 (FIG. 2) of the band to the lower end portion 114 of the band. The elastomeric material of the band forming the elongated force transmission component 110 of this particular embodiment of the invention, has a stiffness (k) of approximately 100,000 Newtons per meter of resilient displacement or stretching.

In this specific embodiment of the invention, the arcuate side surface on the upper rotatable member 1 18 engaged by the right elongated force transmission component 110 has a radius of curvature ($r_1$) of 0.02118 meters. The arcuate side surface on the rotatable member 120 engaged by the right elongated force transmission component 110 has a radius of curvature ($r_3$) of 0.03463 meters. The product of $r_1$ times $r_3$ times k for this specific embodiment of the invention is 73.346 Newton meters.

The design considerations which went into optimizing the efficiency of the apparatus 20 are set forth in Provisional Patent Application Serial No. 60/502,006, filed Sep. 11, 2003 by Antonie J. van den Bogert and entitled "Exotendons for assistance of human locomotion" (Confirmation No. 4670). The disclosure in the aforementioned provisional patent application has been and hereby is incorporated herein in its entirety by this reference thereto. It should be understood that it is believed that it may be preferred to optimize the construction of apparatus 20. However, the apparatus 20 may have a construction which is not optimized.

Although only the apparatus 20 is illustrated in FIG. 2, it should be understood that the apparatus 28 has the same construction as the apparatus 20. Of course, the apparatus 28 is a mirror image of the apparatus 20 so that the apparatus 20 may be connected with the left leg 30 (FIG. 3) of the human body 24. The apparatus 28 includes a left elongated force transmission component, corresponding to the right elongated force transmission component 110. The left apparatus 28 also includes a plurality of rotatable members, corresponding to the rotatable members 118, 120, and 122 of the right apparatus 20.

In the embodiment of the invention illustrated in FIGS. 1-3, the elongated force transmission element 110 is formed by a flexible band polymeric material which can be resiliently stretched. Thus, when a tension force, represented schematically by an arrow 130 in FIG. 4, is applied to the force transmission component 110, the band is resiliently displaced in the manner indicated schematically at 132 in FIG. 4. The band of elastomeric material forming the force transmission component 110 has a stiffness (k) of 100,000 Newtons per meter of displacement. The flexible band of elastomeric material forming the one piece force transmission component 110 has a circular cross sectional configuration. The band of elastomeric material forming the force transmission component 110 may have a different stiffness (k) and/or cross sectional configuration if desired.

When the right leg 22 is being bent in flexion (FIG. 3), the rotatable members 118, 120, and 122 are effective to apply force to the elastomeric material of the elongated force transmission component 110. This results in a resilient stretching of the elongated force transmission component 110 and the storing of energy in the elongated force transmission component. When the leg 28 is moved away from a flexed position, corresponding to the position shown in FIG. 3, toward an extended position, corresponding to a position shown in FIG. 2, the energy stored in the elongated force transmission component 110 is released. As this occurs, the elongated force transmission component 110 resiliently contracts.

Although a one piece elongated force transmission component 110 formed of a resilient polymeric material is utilized in the embodiment of the invention illustrated in FIGS. 1-4, it is contemplated that the elongated force transmission component may have a different construction. For example, an elongated force transmission component 140 (FIG. 5) comprising a plurality of separately formed pieces may be utilized in place of the integrally formed one piece elongated force transmission component 110. The elongated force transmission component 140 includes a cylindrical metal spring 144 which is connected with a cable 146.

Figure 5:
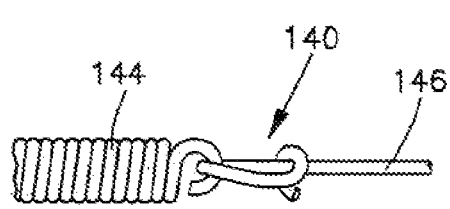
FIG. 5 is a schematic illustration, generally similar to FIG. 4, of another embodiment of the elongated force transmission component which may be utilized in the apparatus of FIG. 3.

Although the elongated force transmission component 140 (FIG. 5) has been illustrated in FIG. 5 as having only a single spring 144 and a single cable 146, it is contemplated that the elongated force transmission component 140 may be formed by a plurality of springs 144 and/or cables 146. The illustrated spring 144 is a metal coil spring which is resiliently extendable by the application of tension force through the cable 146. It is contemplated that a plurality of metal coil springs may be provided in the elongated force transmission component 140.

For example, when the elongated force transmission component 140 (FIG. 5) is used in place of the one piece band of FIG. 4, a first cable may be connected with the pelvic frame member 50 and extend around the anterior side of the rotatable member 118 to a spring 144 disposed midway between the hip frame joint 80 and knee frame joint 82. A second cable may be connected with the spring 144 and extend across the anterior side of the rotatable member 120 to a second spring. The second spring may be disposed midway between the knee frame joint 82 and ankle frame joint 86. A third cable may extend from the second spring across the posterior side of the lower rotatable member 122 to the foot frame member 74.

It should be understood that any desired number of springs 144 and cables 146 may be utilized to form the elongated force transmission component 140. For example, additional springs may be provided at the locations where the cables connect to the pelvic frame member 50 and foot frame member 74. Although a metal coil spring 144 is utilized in the elongated force transmission component 140, it is contemplated that springs having a different construction and formed of a different material may be utilized if desired. For example, a spring formed of a resilient polymeric material and having a construction similar to the construction of a portion of the band of FIG. 4 may be utilized.

The cable 146 (FIG. 5) may be formed of either a polymeric material or metal. The cable 146 may be formed of a polymeric material which is capable of being resiliently stretched so that the force constant (k) of the elongated force transmission component 140, that is, the force per unit of displacement, is a combination of the force constants for the spring 144 and the force constant for the cable 146. Alternatively, the cable 146 may be made of a material which can not be readily stretched, such as stainless steel, and connected to one or more springs. If the cable 146 is formed of stainless steel, it is contemplated that the cable may be sheathed with a suitable polymeric material.

Operation

When the apparatus 20 and 28 has been connected with a human body in the manner illustrated schematically in FIGS. 1-3, the apparatus is effective to substantially reduce muscle forces and the metabolic energy required for an individual to walk. Therefore, by utilizing the apparatus 20 and 28, an individual having large deficits in muscle function may be able to walk. Although it is believed that it will be desired to use both the right apparatus 20 and the left apparatus 28, only one apparatus may be used if desired.

It is contemplated that the use of the apparatus 20 and 28 may result in an overall saving of forty-six percent in joint moment. Most of the benefit of the apparatus 20 is derived from the fact that, in any one leg, the ankle planterflexor and hip flexor moments in walking both reach their peak at the end of the stance phase. That is, at approximately forty percent of a gait cycle. The right and left elastic force transmission systems 38 and 46 are advantageously attached to the human body 24 in a parallel relationship with the muscle and tendons in the human body and therefore assist the muscles and tendons in the human body. This assistance may allow independent locomotion to individuals with large deficits in muscle function.

During a walking gait cycle, the tension force in the right elongated force transmission component 110 varies in the manner illustrated schematically by the dashed line curve 152 in FIG. 6. The manner in which the tension force varies in the corresponding elongated force transmission component in the left elastic force transmission system 46 is indicated by the solid line curves 154 in FIG. 6.

During the portion of the gait cycle between zero and approximately thirteen percent, and from approximately seventy percent to one hundred percent of the gait cycle, there is zero tension force in the right elongated force transmission component 110. If desired, a device may be connected to the framework 34a to take up slack in the force transmission component 110. During the portion of the gait cycle between approximately thirteen percent and approximately seventy percent there is tension force in the elongated force transmission component 110. The tension force in the elongated force transmission component 110 becomes a maximum, as indicated by the curve 152 in FIG. 6, at approximately forty-three percent of the gait cycle.

Variations in the moment (torque) in the joints of the right leg 22 with the gait cycle are illustrated by the curves of the graph in FIG. 7. The manner in which the moments in the hip joint of the right leg 22 vary with the gait cycle without the apparatus 20 is illustrated by the curve 160 in FIG. 7. The manner in which the moments in the knee joint of the right leg 22 vary with the gait cycle without the apparatus 20 is illustrated by a curve 162 in FIG. 7. The manner in which the moment in the ankle joint of the right leg 22 varies with the gait cycle without the apparatus 20 is illustrated by a curve 164 in FIG. 7. It should be understood that the curves 160, 162 and 164 illustrate the manner in which moments vary in joints in the leg 22 in the absence of the apparatus 20.

The manner in which the moments in the hip joint of the right leg 22 vary with a gait cycle when the apparatus 20 is connected with the human body 24 is illustrated by a dashed curve 168 in FIG. 7. Similarly, the manner in which the moment in the ankle joint of the right leg 22 varies with the gait cycle when the apparatus 20 is connected with the human body is illustrated by a dashed curve 170 in FIG. 7. The difference between the curve 160 and the curve 168 in FIG. 7 illustrates the reduction in the moments in the hip joint of a human body when the apparatus 20 is utilized. Similarly, the difference between the curves 164 and 170 illustrate the reduction in the moments in the ankle joint when the apparatus 20 is utilized.

The moment cost of locomotion may be referred to as Cmom. The moment cost of locomotion (Cmom) may be defined as the integral of the absolute value of a joint moment. This integral is calculated for hip, knee and ankle joints and the sum is Cmom. For unassisted walking, Cmom is approximately 14.09 Newton meters during a typical human gait. When an optimal design of the apparatus 20 is utilized, the Cmom is 7.56 Newton Meters or approximately 7.6 Newton meters. Therefore, when an optimal design of the apparatus 20 is utilized, there is a moment cost of locomotion reduction of approximately 46 percent.

The power cost of locomotion may be referred to as Cpwr. The power cost of locomotion (Cpwr) may be defined as the integral of the absolute value of a joint power. This integral is calculated for hip, knee and ankle joints and the sum is Cpwr. For unassisted walking, Cpwr is 20.14 watts during a typical human gait. When an optimal design of the apparatus 20 is utilized, Cpwr is 12.26 watts. Therefore when an optimal design of the apparatus 20 is utilized, there is a power cost of locomotion reduction of approximately 39 percent.

The design considerations which went into minimizing both the moment cost and the power cost of locomotion are set forth in Provisional Patent Application Ser. No. 60/502,006 filed Sep. 11, 2003 by Antonie J. van den Bogert and entitled "Exotendons for assistance of human locomotion" (Confirmation No. 4670). The disclosure in the aforementioned provisional patent application has been and hereby is incorporated herein in its entirety by this reference thereto. It should be understood that it may be preferred to optimize the construction of the apparatus 20. However, the apparatus 20 may have a construction which is not optimized and may have Cmom and Cpwr which are different than the specific costs mentioned herein.

When a gait cycle begins, that is at zero in the graphs of FIGS. 6 and 7, there is no tension force in the right elongated force transmission component 110. At this time, the heel on the foot of the human body is just engaging the ground or support surface. After approximately thirteen percent of the gait cycle has passed, tension forces begin to build in the elongated force transmission component 110 (FIG. 6). As this occurs, the apparatus 20 begins to effect a reduction in the hip joint moments, as shown by the curve 160 in FIG. 7, and the ankle joint moment, as shown by the curve 164 in FIG. 7, to the values illustrated by the curves 168 and 170.

This results in a substantial savings in the muscle force required during the remainder of the gait cycle, until the gait cycle is approximately seventy percent complete. At that time, the elongated force transmission component 110 goes slack and the joint moments return to the same magnitude as they would have in the absence of the apparatus 20. The greatest savings in the muscle effort occurs between approximately forty-two and forty-eight percent of the gait cycle when the moments in the hip joint, as illustrated by the curve 160 in FIG. 7, and the ankle joint, as illustrated by the curve 164 of FIG. 7, are normally the greatest.

Utilization of the apparatus 20 greatly reduces the forces that contribute to joint moments. Minimization of joint moments is advantageous for patients with deficits in muscle strength. For military applications, the reduction in the forces that contribute to joint moments reduces the metabolic energy required for movement to thereby reduce muscle fatigue.

In the graph of FIG. 7, it is considered that joint angles increase during an anterior swing of the distal segment of the joint. Therefore, there is a positive moment arm. This indicates that the elongated force transmission component 110 runs anterior to the hip and knee joints. There is a negative moment arm associated with the ankle joint. This is because the elongated force transmission component 110 runs posterior to the ankle joint.

Use of Motor Power

In the embodiment of the invention described in association with FIGS. 1-7, muscles in the human body 24 were utilized as power sources to supply the forces required in association with the apparatus 20 and 28. In the embodiment of the invention illustrated in FIG. 8, motors are utilized in association with the apparatus 20 and 28 in order to increase the available force for use in association with the apparatus of FIGS. 1-5. Since the embodiment of the invention illustrated in FIG. 8 is generally similar to the embodiments of the invention illustrated in FIGS. 1-5, similar numerals will be utilized to designate similar components, the suffix letter "a" being associated with the numerals of FIG. 8 to avoid confusion.

The apparatus 20a is connected with a right leg 22a on a human body 24a. A corresponding apparatus (not shown) is connected with the left leg of the human body.

The apparatus 20a includes a right framework 34a and a right elastic force transmission system 38a. The right elastic force transmission system 38a cooperates with the framework 34a in the same manner as previously described in conjunction with the embodiment of FIGS. 1-5. The framework 34a includes a frame member 50a which extends around a pelvic or waist portion 52a of the human body 24a. An upper frame member 56a extends downward to and is connected with a lower frame member 64a. The lower frame member 64a is connected with a foot frame member 74a.

The right elastic force transmission system 38a includes an elongated force transmission component 110a which is fixedly connected at an upper end portion 112a to the pelvic frame member 50a. The lower end portion 114a of the elongated force transmission component 110a is fixedly connected to the foot frame member 74a. In addition, the elastic force transmission system 38a includes rotatable members 118a, 120a, and 122a which are disposed in general alignment with joints in the framework 34a and with joints in the human body 24a. The elongated force transmission component 110a spans hip, knee and ankle joints.

In accordance with a feature of the embodiment of the invention illustrated in FIG. 8, a plurality of motors are connected with the framework 34a. Thus, a motor 180 is connected with the pelvic frame member 50a and is operable to move the upper frame member 56a relative to the pelvic frame member. Similarly, a motor 182 is connected with the upper frame member 56a and is operable to move the lower frame member 64a relative to the upper frame member. Although only two motors 180 and 182 have been illustrated schematically in FIG. 8, it should be understood that additional motors may be provided in association with the framework 34a. For example, a motor may be connected with the lower frame member 64a and be operable to move the foot frame member 74a relative to the lower frame member.

The motors 180 and 182 are electric motors. However, hydraulic or pneumatic motors may be utilized. By utilizing the elastic force transmission system 38a in association with the motors 180 and 182, the size of the motors and the size of a power source, such as batteries or a portable generator, for the motors is minimized. This minimizes the overall weight of the apparatus 20a, including the motors 180 and 182 and the power source for the motors.

In the embodiment of the invention illustrated in FIG. 8, the apparatus 20a, including the motors 180 and 182, is utilized to augment the power of muscle in the human body 24a. However, if desired, the apparatus 20a, including the motors 180 and 182, may be used in association with a robot having a configuration which corresponds generally to the configuration of a human body. The apparatus 20a would be used in association with the legs of the robot. If desired, the elastic force transmission system 38a may be disposed beneath the outer system or "skin" of the robot.

It is also contemplated that the apparatus 20 (FIGS. 1-3) may be utilized in association with a lower extremity prosthesis. The apparatus 20 used with the lower extremity prosthesis may or may not include motors corresponding to the motors 180 and 182 of FIG. 8. The prosthesis may be used in association with an above the knee amputee or a below the knee amputee.

When used with a lower extremity prosthesis, the framework 34 would extend from the pelvic or waist region of the human amputee along the remaining portion of the leg of the amputee. The framework 34 would continue along the prosthesis to the foot portion of the prosthesis. The elongated force transmission component 110 would extend from the frame member in the pelvic region of the amputee to the foot portion of the prosthesis. The elastic force transmission system 38 would cooperate with the framework 34, remaining portion of the amputee's leg, and the prosthesis in the same manner as previously explained in conjunction with the embodiment of the invention illustrated in FIGS. 1-3.

Lower Leg

Apparatus

Figure 10:
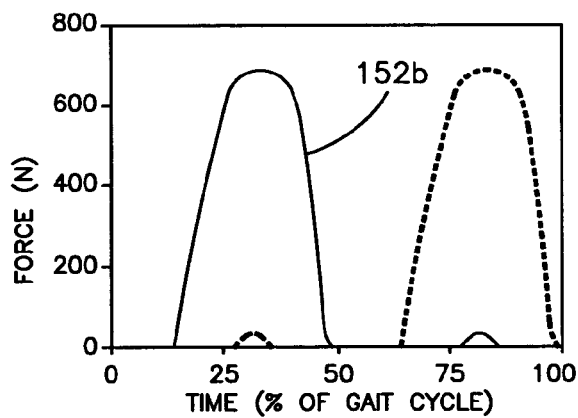
FIG. 10 is a graph, similar to FIG. 6, illustrating the manner in which force varies in elongated force transmission components of the apparatus of FIG. 9 during a walking gait cycle.
Figure 11:
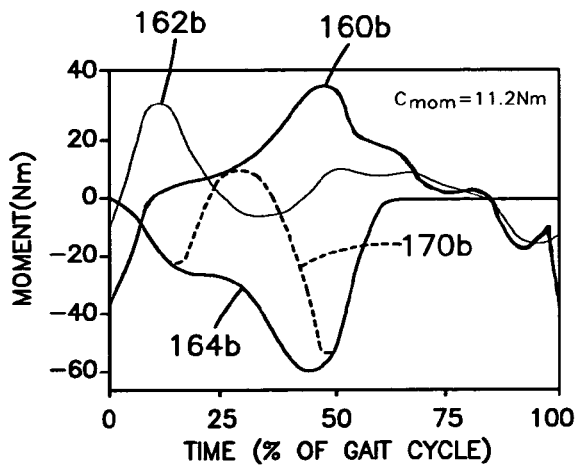
FIG. 11 is a graph, similar to FIG. 7, illustrating the manner in which moment varies in hip, knee, and ankle joints of a human body during a walking gait cycle with and without the apparatus of FIG. 9.

In the embodiment of the invention illustrated in FIGS. 1-3, the frameworks 34 and 42 and the elastic force transmission systems 38 and 46 span three joints associated with each of the legs 22 and 30 of the human body 24. In the embodiment of the invention illustrated in FIG. 9 and the associated graphs of FIGS. 10 and 11, the frameworks and elastic force transmission systems span a single joint in each of the legs of the human body. Since the embodiment of the invention illustrated in FIG. 9 and the associated graphs of FIGS. 10 and 11 is generally similar to the embodiment of the invention illustrated in FIGS. 1-7, similar numerals will be utilized to designate similar components, the suffix letter "b" being associated with the numerals of FIG. 9 to avoid confusion.

An apparatus 20b includes a right framework or exoskeleton 34b which is connectable with a right leg of a human body. A right elastic force transmission system 38b is connected with the right framework 34b. Similarly, an apparatus 28b includes a left framework or exoskeleton 42b which is connected with a left leg of a human body and a left elastic force transmission system 46b.

Figure 9:
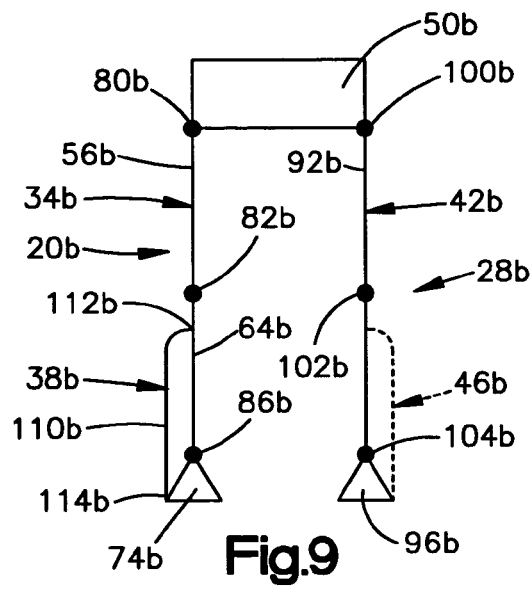
FIG. 9 is a highly schematized illustration, generally similar to FIG. 1, depicting the manner in which an apparatus constructed in accordance with the present invention may be connected with tibial and foot portions of human legs.

In the embodiment of the invention illustrated in FIG. 9, the right framework 34b includes a frame member 50b which extends around the pelvic or waist portion of a human body. An upper frame member 56b is pivotally connected to the pelvic frame member 50b at a hip frame joint 80b. The hip frame joint 80b is disposed adjacent to a hip in a human body with which the framework 44b is connected.

The framework 34b includes a lower frame member 64b. The lower frame member 64b is pivotally connected to the upper frame member 56b at a knee frame joint 82b. A foot frame member 74b is pivotally connected to the lower frame member 64b at an ankle frame joint 86b.

The right elastic force transmission system 38b includes an elastic force transmission component or exotendon 110b. The elastic force transmission component 110b has an upper end portion 112b which is fixedly connected to the lower frame member 64b. A lower end portion 114b of the right elongated force transmission component 110b is fixedly connected at 114b to the foot frame member 74b.

In addition to the elongated force transmission component 110b, the right elastic force transmission 38b includes a rotatable member, corresponding to the lower rotatable member 122 of FIG. 2, around which the elongated force transmission component 110b extends. The elongated force transmission component 110b engages a portion of the rotatable member which is offset in the posterior direction relative to an axis about which the ankle frame joint 86b pivots. Therefore, moments associated with the frame ankle joint 86b are considered to be negative.

The manner in which the force in the elongated force transmission component 110b varies is indicated by a curve 152b in FIG. 10. The manner in which the moments in the right leg vary with and without the apparatus 20b is indicated by the graph in FIG. 11. The manner in which the moment in the hip joint in the human body varies with and without the apparatus 20b is indicated by the curve 160b. The manner in which the moment in the knee joint varies with and without the apparatus 20b is indicated by the curve 162b. It should be noted that the apparatus 20b has no effect on the moment in the hip and knee joints.

The manner in which the moment in the ankle joint varies in the absence of the apparatus 20b is indicated by the curve 164b in FIG. 11. With the apparatus 20b, the moment in the ankle joint varies in the manner indicated by the dashed curve 170b in FIG. 11. The apparatus 20b is effective to reduce ankle joint moments by an amount corresponding to the difference between the curves 164b and 170b.

It should be understood that the apparatus 28b has the same construction and mode of operation as the apparatus 20b. However, the apparatus 28b differs from the apparatus 20b in that the apparatus 28b has been modified for association with the left leg. It should be understood that the apparatus 20b may be used with or without the apparatus 28b. Similarly, it should be understood that the apparatus 28b may be used with or without the apparatus 20b.

Since the right elastic force transmission system 38b is connected with the lower frame member 64b and the foot frame member 74b, the upper frame member 56b and pelvic frame member 50b may be eliminated. If the apparatus 28b is utilized in association with the apparatus 20b, the upper frame member 42b may also be eliminated if desired.

Six Joint Force

Transmission System

Figure 12:
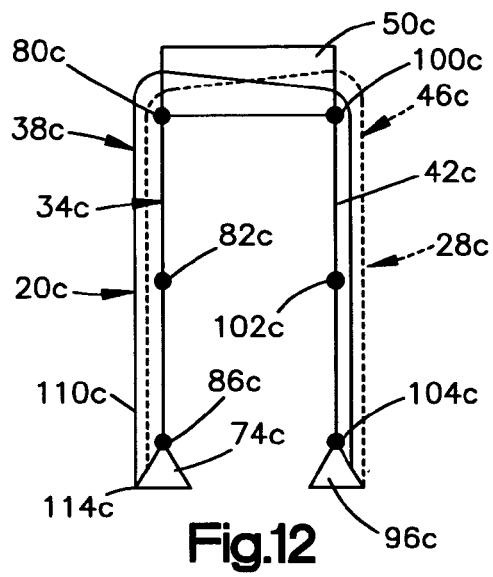
FIG. 12 is a highly schematized illustration, generally similar to FIGS. 1 and 9, depicting the manner in which an apparatus constructed in accordance with the present invention may be connected with legs in a human body.

In the embodiment of the invention illustrated in FIGS. 1-3, each elastic force transmission system 38 and 46 spans three joints, that is, hip, knee and ankle joints. In the embodiment of the invention illustrated in FIG. 12, each elastic force transmission system span six joints. Since the embodiment of the invention illustrated in FIG. 12 is generally similar to the embodiment of the invention illustrated in FIGS. 1-7, similar numerals will be utilized to designate similar components, the suffix letter "c" being associated with the embodiment of the invention illustrated in FIG. 12.

An apparatus 20c (FIG. 12) is connected with a right leg of a human body while an apparatus 28c is connected with a left leg of the human body. Since each of the elastic force transmission systems 38c and 46c are to span three joints in both the right and left legs, both the right and left frameworks 34c and 42c are required.

The right elastic force transmission system 38c includes a right elongated force transmission component or exotendon 110c. The right elongated force transmission component 110c has an end portion 114c which is connected a foot frame member 74c in the right framework 34b. The right elongated force transmission component 110c extends across the pelvic frame member 50c and along the left framework 42c to the left foot frame member 96c. A second end of the right elongated force transmission component 110c is connected to the left foot frame member 96c. Similarly, the elongated force transmission component in the left elastic force transmission system 46c extends from the left foot frame member 96c across the pelvic frame member 50c to the right foot frame member 74c.

The right elastic force transmission system 38c includes three rotatable members or pulleys which are mounted in the right framework 34c in axial alignment with right frame joints 80c, 82c and 86c. In addition the right elastic force transmission system 38c includes three rotatable members or pulleys which are mounted on the left framework 42c in axial alignment with the left frame joints 100c, 102c and 104c. The right elongated force transmission component 110c engages all six of the rotatable members.

The right elongated force transmission component 110c engages the anterior side of the rotatable member (pulley) disposed at the right hip frame joint 80c. The right elongated force transmission component 110c engages the posterior sides of the rotatable members (pulleys) disposed at the right knee frame joint 82c and the right ankle frame joint 86c. The rotatable member (pulley) aligned with the right hip frame joint 80c has a radius which is larger than the radius of the rotatable member aligned with the right knee frame joint 82c and smaller than the radius of the rotatable member aligned with the right ankle frame joint 86c.

The right elongated force transmission component 110c engages the posterior sides of the rotatable members (pulleys) disposed in axial alignment with the left hip frame joint 100c and the left knee frame joint 102c. The right elongated force transmission component may engage either the posterior or anterior side of a rotatable member having a very small radius and disposed in axial alignment with the left ankle frame joint 104c. If desired, the rotatable member may be omitted at the left ankle frame joint 104c.

Similarly, the left elastic force transmission system 46c includes three rotatable members (pulleys) which are mounted on the left framework 42c in axial alignment with the left frame joints 100c, 102c, and 104c. In addition, the left elastic force transmission system 46c includes three rotatable members or pulleys which are mounted on the right framework 34c in axial alignment with the right frame joints 80c, 82c, and 86c. The left elongated force transmission component, corresponding to and having the same construction as the right elongated force transmission component 110c engages all six of the rotatable members.

The left elongated force transmission component engages the anterior side of the rotatable member (pulley) disposed at the left hip frame joint 100c. The left elongated force transmission component engages the posterior sides of the rotatable members (pulleys) disposed at the left knee frame joint 102c and the left ankle frame joint 86c. The rotatable member (pulley) aligned with the left hip frame joint 100c has a radius which is larger than the radius of the rotatable member aligned with the left knee frame joint 102c and smaller than the radius of the rotatable member aligned with the left ankle frame joint 104c.

The left elongated force transmission component, corresponding to the right elongated force transmission component 110c, engages the posterior sides of the rotatable members (pulleys) disposed in axial alignment with the right hip frame joint 80c and the right knee frame joint 82c. The left elongated force transmission component may engage either the posterior or anterior side of a rotatable member having a very small radius and disposed in axial alignment with the right ankle frame joint 86c. If desired, the rotatable member may be omitted at the right ankle frame joint 86c.

Suitable guides (not shown) for the left and right force transmitting components are provided on the posterior side of the pelvic frame member 50c. The guides may include a plurality of pulleys and/or tubular members. The guide for the right force transmitting component 110c includes a pulley disposed adjacent and slightly to the anterior of the axis of the rotatable member (pulley) which is aligned with the left hip frame joint 100c. The guide for the left force transmitting component, corresponding to the right force transmitting component, also includes a pulley disposed adjacent and slightly to the anterior of the axis of the rotatable member aligned with the right hip frame joint 80c.

Figure 13:
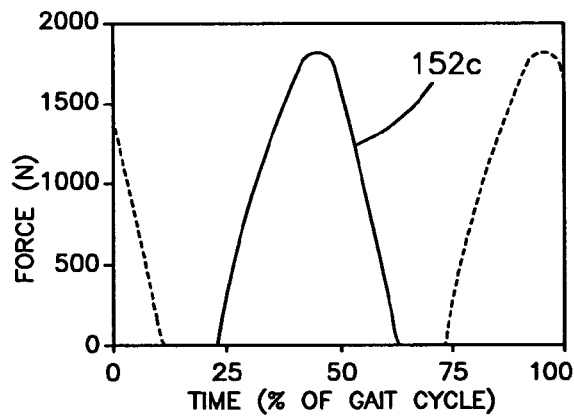
FIG. 13 is a graph, similar to FIGS. 6 and 10, illustrating the manner in which force varies in elongated force transmission components of the apparatus of FIG. 12 during a walking gait cycle.

The manner in which the force in the right elongated force transmission component 110c varies is illustrated by the curve 152c in FIG. 13. The manner in which the moment in the left leg varies during a gait cycle with and without the apparatus 20c and 28c of FIG. 12 is illustrated by the graph of FIG. 14.

Figure 14:
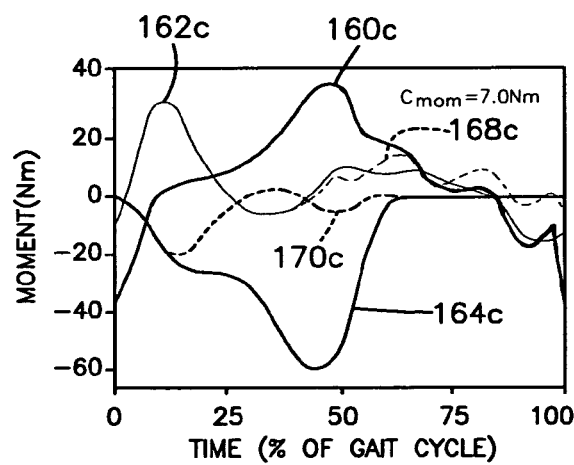
FIG. 14 is a graph, similar to FIGS. 7 and 11, illustrating the manner in which moment varies in the hip, knee, and ankle joints of a human body during a walking gait cycle with and without the apparatus of FIG. 12.

The manner in which the moment in the hip joint varies during a gait cycle in the absence of the apparatus 20c and 28c is illustrated by the curve 160c in FIG. 14. The manner in which the moment in the knee joint varies during a gait cycle in the absence of the apparatus 20c and 28c is indicated by the curve 162c in FIG. 14. In addition, the manner in which the moment in the ankle joint varies during a gait cycle in the absence of the apparatus 20c and 28c is indicated by the curve 164c in FIG. 14.

When the apparatus 20c and 28c is used, in the manner illustrated schematically in FIG. 12, the moment in the hip joint varies during a gait cycle in the manner indicated by the curve 168c in FIG. 14. It should be noted that for a portion of its length, the curve 168c overlies the curve 162c. The manner in which the moment in the ankle joint varies during a gait cycle when the apparatus 20c and 28c is utilized is indicated by the curve 170c in FIG. 14.

The performance of the apparatus 20c (FIG. 12) may be varied by varying the radii of the arcuate side on the rotatable members which engage the force transmission component 110c. In addition, the performance of the apparatus 20c may be varied by varying the stiffness, that is, the spring force constant, of the elastic force transmission system 38c.

It is believed that the circular arcuate side surface disposed on the rotatable member aligned with the right hip frame joint 80c and engaged by the elongated force transmission component 110c should have a radius which is greater than the radius of the circular arcuate side surface disposed on the rotatable member aligned with the right knee frame joint 82c and engaged by the elongated force transmission component 110c. It is also believed that the circular arcuate side surface disposed on the rotatable member aligned with the right hip frame joint 80c and engaged by the elongated force transmission component 110c should have a radius which is less than a radius of the circular arcuate surface disposed on the lower rotatable member aligned with the right ankle frame joint 86c and engaged by the elastic force transmission component 110c. However, it should be understood that the apparatus 20c may be constructed with a different relationship between the radii on the rotatable members if the performance of the apparatus 20c is acceptable.

It is believed that the performance of the apparatus 20c may be made very satisfactory by having the product of the radius of curvature for the arcuate side surface disposed on the rotatable member aligned with the hip frame joint 80c ($r_1$), the radius of curvature for the arcuate surface on the rotatable member aligned with the ankle frame joint 86c ($r_3$), and the stiffness of the elastic force transmission system 38c (k) equal to between fifty-one (51) and ninety-five (95) Newton meters. This may be expressed by an equation of: $(r_1) \cdot (r_3) \cdot (k) = 51$ to 95 Newton meters. It is believed that the efficiency of the apparatus 20c is optimized when the product of the radius of curvature of the arcuate surface on the rotatable member aligned with the hip frame joint 80c ($r_1$) and the radius of curvature of the arcuate surface on the lower rotatable member aligned with the ankle frame joint 86c ($r_3$) and the stiffness or spring force constant of the elastic force transmission system 38c (k) is equal to approximately 73 Newton meters. Although the optimal relationship between the product of $(r_1) \cdot (r_3) \cdot (k)$ is approximately 73 Newton meters, it should be understood that the apparatus 20c is still functionally satisfactory and provides significant advantages when the product is somewhat greater than or less than seventy-three Newton meters.

Two Six Joint Force

Transmission Systems

Figure 15:
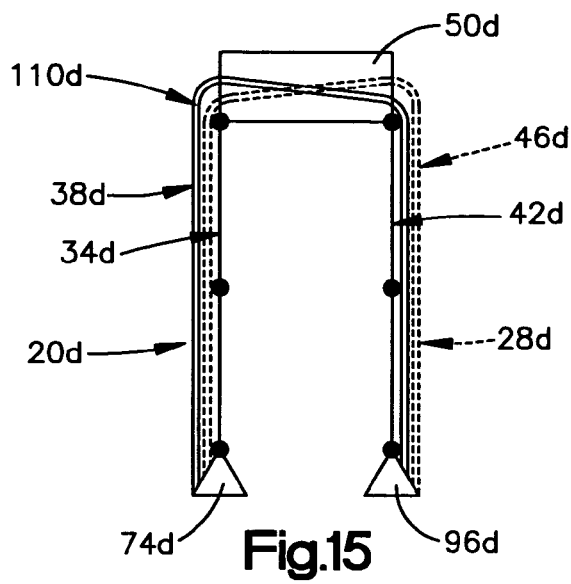
FIG. 15 is a highly schematized illustration, generally similar to FIGS. 1, 9 and 12, depicting the manner in which an apparatus constructed in accordance with the present invention may be connected with legs in a human body.

In the embodiment illustrated in FIG. 15 and in the associated graphs 16 and 17, there are four elastic force transmission systems associated with a framework connected with the legs of a human body. Since the embodiment of the invention illustrated in FIG. 15 is generally similar to the embodiments of the invention illustrated in FIGS. 1-14, similar numerals will be utilized to designate similar components, the suffix letter "d" being associated with the numerals of FIG. 15 to avoid confusion.

An apparatus 20d is associated with the right leg of a human body. An apparatus 28d is associated with a left leg of a human body. The apparatus 20d includes a framework 34d connected with the right leg of a human body. A second framework 42d is associated with the left leg of the human body. A right elastic force transmission system 38d, shown in solid lines in FIG. 15, is connected with both frameworks 34d and 42d. A left elastic force transmission system 46d, shown in dashed lines in FIG. 15, is connected with the left framework 42d and the right framework 34d.

The right elastic force transmission system 38d includes a pair of elongated force transmission components 110d. The right elongated force transmission components 110d are connected with the right foot frame member 74d. The right elongated force transmission components 110d extend across two sets of rotatable members connected with frame joints in the manner previously explained in conjunction with the embodiment of the invention illustrated in FIGS. 1-7.

In addition, the elongated force transmission components 110d extend across the frame member 50d which extends around the pelvic or waist portion of the human body. The ends of the elongated force transmission components 110d are connected to the left foot frame member 96d. The left elastic force transmission system 46d has the same construction as the right elastic force transmission system 38d and is connected with the frameworks 34d and 42d in the same manner.

Figure 16:
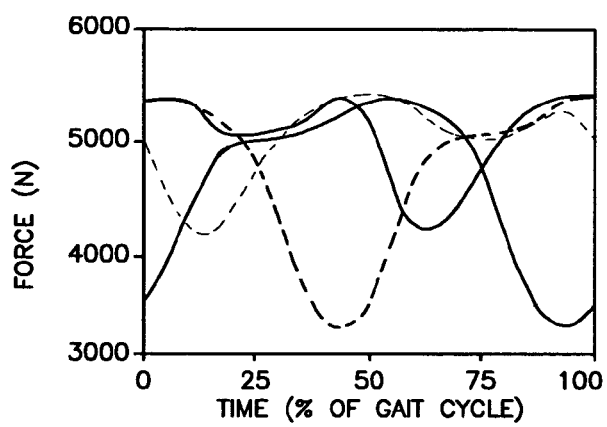
FIG. 16 is a graph, similar to FIGS. 6, 10, and 13, illustrating the manner in which force varies in elongated force transmission components of the apparatus of FIG. 15 during a walking gait cycle.
Figure 17:
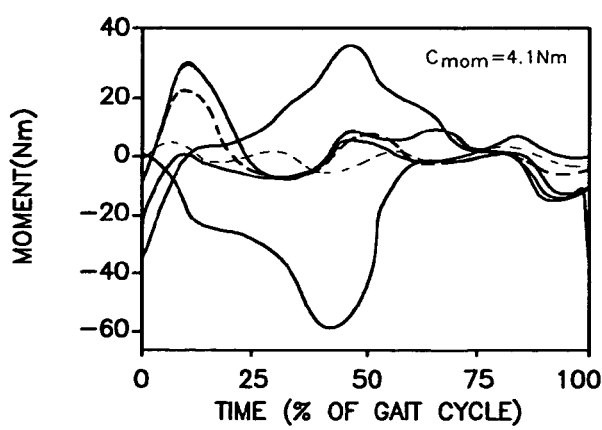
FIG. 17 is a graph, similar to FIGS. 7, 11 and 14, illustrating the manner in which moment varies in the hip, knee, and ankle joints of a human body during a walking gait cycle with and without the apparatus of FIG. 15.

The manner in which the force varies in the elongated force transmission components of the right and left elastic force transmission systems 38d and 46d is illustrated in the graph of FIG. 16. The manner in which moments vary in the joints of the right leg are indicated by the graph of FIG. 17.

Optimized Systems

Optimized moment cost apparatus for the embodiments of the invention illustrated in FIGS. 1-17 have rotatable members, which may be pulleys, with the radii (r) indicated in the following Table 1.

TABLE 1

| Moment optimized | RIGHT | | | LEFT | | | $L_{slack}$ (mm) | Cmom (N m) | $C_{pow}$ (W) |
| --- | --- | --- | --- | --- | --- | --- | --- | --- | --- |
| | $r_{hip}$ (mm) | $r_{knee}$ (mm) | $r_{ankle}$ (mm) | $r_{hip}$ (mm) | $r_{knee}$ (mm) | $r_{ankle}$ (mm) | | | |
| FIGS. 1-7 | 21.18 | 0.23 | −34.63 | 21.18 | 0.23 | −34.63 | −7.77 | 7.56 | 12.26 |
| FIGS. 9-11 | N/A | | −60.20 | N/A | | −60.20 | 6.54 | 11.14 | 18.68 |
| FIGS. 12-14 | 21.33 | −0.61 | −34.31 | −8.08 | −5.63 | 0.00 | −4.04 | 7.04 | 12.09 |
| FIGS. 15-17 | 7.77 | 1.25 | −23.45 | −5.24 | 0.65 | 21.91 | −24.34 | 4.08 | 5.66 |
| | −7.60 | −11.92 | −15.68 | 10.70 | −4.37 | −5.88 | −11.53 | | |

In the embodiment of FIGS. 1-7, the right and left elastic force transmission systems 38 and 46 have the same construction. Therefore, the rotatable members adjacent to the hip frame joints 80 and 100 (FIG. 1) have the same radii ($r_{hip}$) of 21.18 millimeters (Table 1). Similarly, the rotatable members adjacent to the knee frame joints 82 and 102 (FIG. 1) have the same radii ($r_{knee}$) of 0.23 millimeters (Table 1). The rotatable members adjacent to the ankle frame joints have the same radii ($r_{ankle}$) of 34.63 millimeters.

The optimum radii for the rotatable members have been set forth in Table 1 for use in an optimum moment cost apparatus with an elastic force transmission system having a stiffness (k) of 100,000 Newtons per meter of displacement. If the elastic force transmission systems associated with the various embodiments of the invention illustrated in FIGS. 1-12 have a different stiffness, the optimum radii for an optimum moment cost apparatus will be different then set forth in Table 1.

Although the rotatable member radii set forth in Table 1 may be preferred, at least in an optimum moment cost apparatus when the associated elastic force transmission systems have a stiffness of 100,000 Newtons per meter of displacement, different radii may be used if desired. Although rotatable member radii which are different than the radii set forth in Table 1 may not be optimum, the apparatus having elastic force transmission systems with radii which are different than set forth in Table 1 will still provide significant assistance to human body movement. Therefore, the various embodiments of the invention are not limited to use with rotatable members having the specific radii set forth in Table 1. It is contemplated that embodiments of the invention which have not been optimized will be used in and will provides desired assistance to human body movement.

Optimized power cost apparatus for the embodiments of the invention illustrated in FIGS. 1-17 have rotatable members, which may be pulleys, with the radii (r) indicated in the following Table 2.

In the embodiment of FIGS. 1-7, the right and left elastic force transmission systems 38 and 46 have the same construction. Therefore, the rotatable members adjacent to the hip frame joints 80 and 100 (FIG. 1) have the same radii (r) of 33.06 millimeters (Table 2). Similarly, the rotatable members adjacent to the knee frame joints 82 and 102 (FIG. 1) have the same radii ($r_{knee}$) of 12.76 millimeters (Table 2). The rotatable members adjacent to the ankle frame joints have the same radii ($r_{ankle}$) of 32.85 millimeters.

The optimum radii for the rotatable members have been set forth in Table 2 for use in an optimum power cost apparatus with an elastic force transmission system having a stiffness (k) of 100,000 Newtons per meter of displacement. If the elastic force transmission systems associated with the various embodiments of the invention illustrated in FIGS. 1-12 have a different stiffness, the optimum radii for an optimum power cost apparatus will be different then set forth in Table 2.

It is contemplated that the moment cost optimized apparatus associated with Table 1 will reduce human muscle force, when used with the apparatus of FIGS. 1-7 and 9-12, more than the power cost optimized apparatus associated with Table 2. However, it is contemplated that the power cost optimized apparatus associated with Table 2 will reduce power required when used with the apparatus of FIG. 8, powered exoskeletons, and robots.

Although the rotatable member radii set forth in Table 2 may be preferred, at least in an optimum power cost apparatus when the associated elastic force transmission systems have a stiffness of 100,000 Newtons per meter of displacement, different radii may be used if desired. Although rotatable member radii which are different than the radii set forth in Table 2 may not be optimum, the apparatus having elastic force transmission systems with radii which are different than set forth in Table 2 will still provide significant assistance to human body movement. Therefore, the various embodiments of the invention are not limited to use with rotatable members having the specific radii set forth in Table 2. It is contemplated that embodiments of the invention which have not been optimized will be used in and will provide desired assistance to human body movement.

TABLE 2

| Power optimized | RIGHT | | | LEFT | | | $L_{slack}$ (mm) | $C_{mom}$ (N m) | $C_{pow}$ (W) |
| --- | --- | --- | --- | --- | --- | --- | --- | --- | --- |
| | hip (mm) | knee (mm) | ankle (mm) | hip (mm) | knee (mm) | ankle (mm) | | | |
| FIGS. 1-7 | 33.06 | 12.76 | −32.85 | 33.06 | 12.76 | −32.85 | −1.55 | 9.06 | 10.64 |
| FIGS. 9-11 | N/A | | −49.83 | N/A | | | 1.04 | 11.97 | 18.18 |
| FIGS. 12-14 | −10.05 | −2.74 | 13.79 | 10.87 | 3.22 | −16.12 | −89.62 | 7.57 | 9.73 |
| FIGS. 15-17 | −4.69 | −9.77 | −19.04 | 10.89 | −5.67 | −0.17 | −12.30 | 4.37 | 5.18 |
| | 7.47 | 3.98 | −25.11 | −6.82 | −2.18 | 24.18 | −75.33 | | |

Conclusion

In view of the foregoing description, it is apparent that the present invention provides a new and improved apparatus 20 for use in assisting human body movement. The apparatus 20 includes a framework 34 which is connectable with the human body 24 and an elastic force transmission system 38 which is connected with the framework. The elastic force transmission system 38 stores energy during a first portion of movement of human body 24 and releases the stored energy during a second portion of the movement of the human body. The elastic force transmission system 38 may include an elongated force transmission component 110 which is resiliently extendable to store energy. The elongated force transmission component 110 may be resiliently contractible to release the stored energy. The elongated force transmission component 110 may span one or more joints in the human body.

The framework 34 may include a plurality of frame members 50, 56, 64, and 74 which are interconnected by a plurality of frame joints 80, 82, and 86 which are disposed adjacent to joints in the human body. A plurality of rotatable members 118, 120 and 122 may be connected with the framework 34 and disposed adjacent to the frame joints. The elongated force transmission component 110 may be connected with the framework and may engage arcuate surfaces on the rotatable members 118, 120, and 122.

The elongated force transmission component 110 may be offset in an anterior direction at locations where the elongated force transmission component engages arcuate surfaces on first and second rotatable members 118 and 120. The elongated force transmission component 110 may be offset in a posterior direction at a location where the force transmission component engages one or more additional rotatable member 122. A first rotatable member 118 may have a radius which is greater than the radius of a second rotatable member 120 and less than the radius of a third rotatable member 122. Of course, a greater or lesser number of rotatable members having radii with any desired size relationship may be used.

Although the apparatus 20 may be utilized with many different portions of a human body, such as an arm, the apparatus may advantageously be used in association with a leg 22. When this is the case, a first rotatable member 118 may be adjacent to a hip joint in the human body 24. A second rotatable member 120 may be adjacent to a knee joint in the leg 22 of the human body. A third rotatable member 122 may be disposed adjacent to an ankle joint in the leg 22 of the human body 24. It is believed that the arcuate surfaces on the rotatable members 118, 120 and 122 may be sized such that the product of the radii of the first and third arcuate surfaces times the stiffness of the force transmission system 38 is equal to between 51 and 95 Newton meters. However, different embodiments of the invention may utilize different numbers of rotatable members and have a different relationship between rotatable member size and force transmission system stiffness.

The present invention includes many different features which may be utilized either separately or in various combinations with each other. For example, the rotatable members 118, 120 and 122 may be sized and located in different ways. The elongated force transmission component 110 may have any one of many different constructions. The apparatus 20 may be used with only one leg 22 and/or arm. Alternatively, the apparatus 20, 28 may be used with both legs and/or arms. It should be understood that features of the invention may be used in ways or in combinations other than the foregoing examples.

Having described the invention, the following is claimed:

1. An apparatus for use in assisting movement of a leg in a human body, said apparatus comprising a framework which includes a plurality of frame members that are connected with each other at a plurality of frame joints, said plurality of frame members including a first frame member which is connected with a second frame member at a first frame joint of said plurality of frame joints, said first frame member being connectable with a pelvic portion of the human body, said second frame member being disposed along a femoral portion of the leg of the human body, said first frame joint being disposed adjacent to a hip joint associated with the pelvic portion of the human body and the femoral portion of the leg of the human body, a third frame member of said plurality of frame members being disposed along a tibial portion of the leg of the human body, said third frame member being connected with said second frame member at a second frame joint of said plurality of frame joints, said second frame joint being disposed adjacent to a knee joint in the leg of the human body, a fourth frame member of said plurality of frame members being connectable with a foot portion of the leg of the human body, said fourth frame member being connected with said third frame member at a third frame joint of said plurality of frame joints, said third frame joint being disposed adjacent to an ankle joint in the leg of the human body, and an elastic force transmission system connected with said framework to store energy during a first portion of movement of the leg of the human body and for releasing energy during a second portion of movement of the leg of the human body, said elastic force transmission system spans the hip, knee and ankle joints in the human body, said elastic force transmission system has a first anchor portion connected with said first frame member and a second anchor portion connected with said fourth frame member.

2. An apparatus as set forth in claim 1 wherein said elastic force transmission system includes an elongated force transmission component which extends along said second and third frame members, a first portion of said elongated force transmission component being offset in an anterior direction from an axis extending through the first frame joint, a second portion of said elongated force transmission component being offset in a posterior direction from an axis extending through said third frame joint, said elongated force transmission component being resiliently extendable under the influence of force transmitted through said framework to said elongated force transmission component during the first portion of movement of the leg of the human body, said elongated force transmission component being resiliently contractible to transmit force from said elongated force transmission component to said framework during the second portion of movement of the leg of the human body.

3. An apparatus as set forth in claim 2 wherein elongated force transmission component is integrally formed as one piece.

4. An apparatus as set forth in claim 2 wherein said elongated force transmission component includes a plurality of pieces which are interconnected.

5. An apparatus as set forth in claim 2 wherein said elastic force transmission system includes a first rotatable member which is connected with said framework adjacent to said first frame joint, a second rotatable member which is connected with said framework adjacent to said second frame joint, and a third rotatable member which is connected to said framework adjacent to said third frame joint, said first portion of said elongated force transmission component being disposed in engagement with and being effective to rotate said first rotatable member during at least a portion of the resilient extension and contraction of said elongated force transmission component, said first portion of said elongated force transmission component being disposed in engagement with and being effective to rotate said second rotatable member during at least a portion of the resilient extension and contraction of said elongated force transmission component, said second portion of said elongated force transmission component being disposed in engagement with and being effective to rotate said third rotatable member during at least a portion of the resilient extension and contraction of said elongated force transmission component.

6. An apparatus as set forth in claim 2 wherein said force transmission system includes a first member which is connected with said framework adjacent to said first frame joint, said first member has a first arcuate surface which engages said first portion of said elongated force transmission component and which has a first radius of curvature, a second member which is connected with said framework adjacent to said second frame joint, said second member has a second arcuate surface which engages said first portion of said elongated force transmission component and which has a second radius of curvature which is smaller than said first radius of curvature, a third member which is connected with said framework adjacent to said third frame joint, said third member has a third arcuate surface which engages said second portion of said elongated force transmission component and which has a third radius of curvature which is larger than said first radius of curvature.

7. An apparatus as set forth in claim 6 wherein said first, second and third members are pulleys which are rotatable relative to said framework during extension and contraction of said elongated force transmission component.

8. An apparatus as set forth in claim 6 wherein said elastic force transmission system has a stiffness of k, said first arcuate surface has a radius of $r_1$, said second arcuate surface has a radius of $r_2$, and said third arcuate surface has a radius of $r_3$, said first and third arcuate surfaces being sized such that the product of $(r_1) \cdot (r_3) \cdot (k)$ is equal to between 51 and 95 Newton meters.

9. An apparatus as set forth in claim 1 further including a plurality of motors which are connected with said framework to provide force which assists in movement of the leg in the human body.

10. An apparatus as set forth in claim 1 wherein said elastic force transmission system includes a band which is formed of elastomeric material and is resiliently extended under the influence of force transmitted from said framework.

11. An apparatus as set forth in claim 1 wherein said elastic force transmission system includes a metal spring which is resiliently extended under the influence of force transmitted from said framework.

12. An apparatus as set forth in claim 11 wherein said elastic force transmission system includes a cable connected with said metal spring.

13. An apparatus for use in assisting movement of a leg in a human body, said apparatus comprising a framework which is connectable with the leg in the human body, and an elastic force transmission system connected with said framework to store energy during a first portion of the movement of the leg and for releasing energy during a second portion of the movement of the leg, said elastic force transmission system has a stiffness of k, said elastic force transmission system includes a plurality of rotatable members which are connected with said framework, said plurality of rotatable members includes a first member having a first arcuate surface with a radius of $r_1$, a second member having a second arcuate surface with a radius of $r_2$, and a third member having a third arcuate surface with a radius of $r_3$, and an elongated force transmission component which is connected with said framework and engages said arcuate surfaces on said first second, and third rotatable members, said first and third arcuate surfaces being sized such that the product of $(r_1) \cdot (r_3) \cdot (k)$ is equal to between 51 and 91 Newton meters.

14. An apparatus as set forth in claim 13 wherein said radius $r_1$ of said first arcuate surface is larger than said radius $r_2$ of said second arcuate surface and is smaller than said radius $r_3$ of said third arcuate surface.

15. An apparatus as set forth in claim 13 wherein said elongated force transmission component engages portions of said first and second arcuate surfaces which are offset in a first direction from axes about which said first and second members are rotatable, said elongated force transmission component engages a portion of said third arcuate surface which is offset in a second direction from an axis about which said third member rotates.

16. An apparatus as set forth in claim 13 further including a plurality of motors connected with said framework to provide force which assists in movement of the human body.

17. An apparatus as set forth in claim 13 wherein each of said rotatable members is a circular pulley which is rotatable under the influence of force transmitted from said elongated force transmission component.

18. An apparatus as set forth in claim 13 wherein said elongated force transmission component is at least partially formed of elastomeric material which is resiliently extended under the influence of force transmitted from said framework.

19. An apparatus as set forth in claim 13 wherein said elongated force transmission component includes a metal spring which is resiliently extended under the influence of force transmitted from said framework during the first portion of movement of the leg.

20. An apparatus as set forth in claim 13 wherein said elongated force transmission component includes a metal cable which is connected with a spring.

21. An apparatus as set forth in claim 13 wherein said framework includes a plurality of frame members and a plurality of frame joints which interconnect said frame members and which are disposed adjacent to joints in the leg.

22. An apparatus as set forth in claim 13 wherein said first arcuate surface has a radius $r_1$ of between fifteen and twenty-seven millimeters and said third arcuate surface has a radius $r_3$ of between twenty-four millimeters and forty-five millimeters.

23. An apparatus as set forth in claim 13 wherein said elastic force transmission system has a stiffness (k) of approximately one hundred thousand Newtons per meter, said first member has a radius ($r_1$) of approximately twenty-one millimeters, and said third member has a radius of approximately thirty-five millimeters.

24. An apparatus as set forth in claim 13 wherein said elongated force transmission component has a first and second end portions which are connected with said framework.

25. An apparatus as set forth in claim 13 further including a second framework which is connectable with a second leg in the human body, and a second elastic force transmission system connected with said second framework to store energy during a first portion of the movement of the second leg and for releasing energy during a second portion of the movement of the second leg, said second elastic force transmission system has a stiffness of $k_2$, said second elastic force transmission system includes a second plurality of rotatable members which are connected with said second framework, said second plurality of rotatable members includes a fourth member having a fourth arcuate surface with a radius of $r_4$, a fifth member having a fifth arcuate surface with a radius of $r_5$, and a sixth member having a sixth arcuate surface with a radius of $r_6$, and a second elongated force transmission component which is connected with said second framework and engages said arcuate surfaces on said fourth, fifth, and sixth rotatable members, said fourth and sixth arcuate surfaces being sized such that the product of $(r_4) \cdot (r_6) \cdot (k_2)$ is equal to between 51 and 91 Newton meters.

26. An apparatus for use in assisting in movement of first and second legs in a human body, said apparatus comprising a framework which includes a plurality of frame members that are connected with each other at a plurality of frame joints, said plurality of frame members including a first frame member which is connectable with a pelvic portion of the human body, a second frame member which extends along a femoral portion of the first leg of the human body, said first and second frame members being interconnected by a first frame joint which is disposed adjacent to a first hip joint associated with the pelvic portion of the human body and the femoral portion of the first leg of the human body, a third frame member which extends along a tibial portion of the first leg of the human body, said second and third frame members being interconnected by a second frame joint which is disposed adjacent to a knee joint in the first leg of the human body, a fourth frame member which is connectable with a foot portion of the first leg of the human body, said third and fourth frame members being interconnected by a third frame joint which is disposed adjacent to an ankle joint in the first leg of the human body, a fifth frame member which extends along a femoral portion of the second leg of the human body, said first and fifth frame members being interconnected by a fourth frame joint which is disposed adjacent to a second hip joint associated with the pelvic portion of the human body and the femoral portion of the second leg of the human body, a sixth frame member which extends along a tibial portion of the second leg of the human body, said fifth and sixth frame members being interconnected by a fifth frame joint which is disposed adjacent to a knee joint in the second leg of the human body, and a seventh frame member which is connectable with a foot portion of the second leg of the human body, said sixth and seventh frame members being interconnected by a sixth frame joint which is disposed adjacent to an ankle joint in the second leg of the human body, and first and second elastic force transmission systems connected with said framework to store energy and to release energy during movement of the first and second legs of the human body, said first elastic force transmission system includes a plurality of rotatable members which are connected with said framework, said plurality of rotatable members includes a first rotatable member which is disposed adjacent to said first frame joint, a second rotatable member which is disposed adjacent to said second frame joint, and a third rotatable member which is disposed adjacent to said third frame joint, said second elastic force transmission system includes a fourth rotatable member which is disposed adjacent to said fourth frame joint, a fifth rotatable member which is disposed adjacent to said fifth frame joint, and a sixth rotatable member which is disposed adjacent to said sixth frame joint, said first elastic force transmission system includes a first elongated force transmission component which is connected with said frame work and engages arcuate surfaces on said first, second and third rotatable members, said second elastic force transmission system includes a second elongated force transmission component which is connected with said framework and engages arcuate surfaces on said fourth, fifth and sixth rotatable members.

27. An apparatus as set forth in claim 26 wherein said first elongated force transmission component includes a first portion which engages said arcuate surface on said first rotatable member and is offset in an anterior direction relative to the human body from an axis about which said first rotatable member rotates, said first elongated force transmission component includes a second potion which engages said arcuate surface on said second rotatable member and is offset in an anterior direction relative to the human body from an axis about which said second rotatable member rotates, said first elongated force transmission component includes a third portion which engages said arcuate surface on said third rotatable member and is offset in a posterior direction relative to the human body from an axis about which said third rotatable member rotates, said second elongated force transmission component includes a first portion which engages said arcuate surface on said fourth rotatable member and is offset in an anterior direction relative to the human body from an axis about which said fourth rotatable member rotates, said second elongated force transmission component includes a second portion which engages said arcuate surface on said fifth rotatable member and is offset in an anterior direction relative to the human body from an axis about which said fifth rotatable member rotates, said second elongated force transmission component includes a third portion which engages said arcuate surface on said sixth rotatable member and is offset in a posterior direction relative to the human body from an axis about which said sixth rotatable member rotates.

28. An apparatus as set forth in claim 26 wherein said first elongated force transmission component has a first end portion which is connected to said first frame member and a second end portion which is connected to said fourth frame member, said second elongated force transmission component has a first end portion which is connected to said first frame member and a second end portion which is connected to said seventh frame member.

29. An apparatus as set forth in claim 26 wherein said first elongated force transmission component has a first end portion which is connected to said fourth frame member and a second end portion which is connected to said seventh frame member, said second elongated force transmission component has a first end portion connected to said seventh frame member and a second end portion connected to said fourth frame member.

30. An apparatus as set forth in claim 26 wherein said first rotatable member has an arcuate surface which has a first radius and engages a first portion of said first elongated force transmission component, said second rotatable member has an arcuate surface which has a second radius and engages a second portion of said first elongated force transmission component, said third rotatable member has an arcuate surface which has a third radius and engages a third portion of said first elongated force transmission component, said first radius being larger than said second radius and smaller than said third radius, said fourth rotatable member has an arcuate surface which has a fourth radius and engages a first portion of said second elongated force transmission component, said fifth rotatable member has an arcuate surface which has a fifth radius and engages a second portion of said second elongated force transmission component, said sixth rotatable member has an arcuate surface which has a sixth radius and engages a third portion of said second elongated force transmission component, said fourth radius being larger than said fifth radius and smaller than said sixth radius.

31. An apparatus as set forth in claim 26 wherein said first elongated force transmission component includes a first band which is formed of elastomeric material and is resiliently extended under the influence of force transmitted from said framework, said second elongated force transmission component includes a second band which is formed of elastomeric material and is resiliently extended under the influence of force transmitted from said framework.

32. An apparatus as set forth in claim 26 wherein said first and second elongated force transmission components include a single band of elastomeric material which extends across said first frame member and engages said first, second, third, fourth, fifth, and sixth rotatable members.

33. An apparatus as set forth in claim 26 wherein said first elongated force transmission component includes a first metal spring which is resiliently extended under the influence of force transmitted from said framework, said second elongated force transmission component includes a second metal spring which is resiliently extended under the influence of force transmitted from said framework.

34. An apparatus as set forth in claim 33 wherein said first elongated force transmission component includes a first cable which is connected with said first spring and said second elongated force transmission component includes a second cable which is connected with said second spring.

35. An apparatus as set forth in claim 26 further including a plurality of motors connected with said framework to provide force which assists in movement of the human body.

36. An apparatus as set forth in claim 26 wherein said first rotatable member has a first arcuate surface which engages a first portion of said first elongated force transmission component and has a first radius ($r_1$), said second rotatable member has a second arcuate surface which engages a second portion of said first elongated force transmission component and has a second radius ($r_2$), said third rotatable member has a third arcuate surface which engages a third portion of said first elongated force transmission component and has a third radius ($r_3$), said first elastic force transmission system has a first stiffness if $K_1$, said first and third arcuate surfaces being sized such that the product of $(r_1) \cdot (r_3) \cdot (k_1)$ is equal to between 51 and 91 Newton meters, said fourth rotatable member has a fourth arcuate surface which engages a first portion of said second elongated force transmission component and has a fourth radius ($r_4$), said fifth rotatable member has a fifth arcuate surface which engages a second portion of said second elongated force transmission component and has a fifth radius ($r_5$), said sixth rotatable member has a sixth arcuate surface which engages a third portion of said second elongated force transmission component and has a sixth radius ($r_6$), said second elastic force transmission system has a second stiffness of $K_2$, said fourth and sixth arcuate surfaces being sized such that the product of $(r_4) \cdot (r_6) \cdot (k_2)$ is equal to between 51 and 91 Newton meters.

37. An apparatus for use in assisting human body movement, said apparatus comprising a framework which includes a plurality of frame members which are connected with each other at a plurality of frame joints, said plurality of frame members being connectable with the human body with said frame joints adjacent to joints in the human body, and an elastic force transmission system connected with said frame members to store energy during a first portion of the movement of the human body and for releasing the stored energy during a second portion of the movement of the human body, said elastic force transmission system includes an elongated force transmission component which extends along said framework, said elongated force transmission component being resiliently extendable under the influence of force transmitted through said framework to said elongated force transmission component during the first portion of the movement of the human body, said elongated force transmission component being resiliently contractible to transmit force from said elongated force transmission component to said framework during the second portion of the movement of the human body, said elastic force transmission system includes a first pulley having an arcuate surface with a radius of $r_1$ and disposed adjacent to a first frame joint of said plurality of frame joints, a second pulley having an arcuate surface with a radius of $r_2$ and disposed adjacent to a second frame joint of said plurality of frame joints, and a third pulley having an arcuate surface with a radius of $r_3$, said first, second and third pulleys being connected with and rotatable relative to said framework, said elastic force transmission system having a stiffness of k, said first and third arcuate surfaces being sized such that the product of $(r_1) \cdot (r_3) \cdot (k)$ is equal to between 51 and 95 Newton meters, said elongated force transmission component being disposed in engagement with said arcuate surfaces on said first, second and third pulleys.

38. An apparatus as set forth in claim 37 wherein said first pulley is disposed adjacent to a first frame joint which connects a first frame member with a second frame member, said first frame member being connectable with a pelvic portion of the human body and said second frame member being disposed adjacent to a femoral portion of the human body, said first and second frame members being interconnected by said first frame joint, said first frame joint and said first pulley being disposed adjacent to a hip joint in the human body when said first frame member is connected with the pelvic portion of the human body and said second frame member is disposed adjacent to the femoral portion of the human body, said second pulley is disposed adjacent to a second frame joint which connects said second frame member with a third frame member, said third frame member being disposed adjacent to a tibial portion of the human body, said second and third frame members being interconnected by a second frame joint of said plurality of frame joints, said second frame joint and said second pulley being disposed adjacent to a knee joint in the human body when said second frame member is adjacent to the femoral portion of the human body and said third frame member is adjacent to the tibial portion of the human body, said third pulley is disposed adjacent to said third frame joint which connects said third frame member with said fourth frame member, said fourth frame member being connectable with a foot portion of the human body, said third and fourth frame members being interconnected by a third frame joint of said plurality of frame joints, said third frame joint and said third pulley being disposed adjacent to an ankle joint in the human body when said third frame member is adjacent to the tibial portion of the human body and said fourth frame member is connected with the foot portion of the human body.

39. An apparatus as set forth in claim 37 wherein said elongated force transmission component includes a band which is formed of elastomeric material and is resiliently extended under the influence of force transmitted from said framework.

40. An apparatus as set forth in claim 37 wherein said elongated force transmission component includes a metal spring which is resiliently extended under the influence of force transmitted from said framework.

41. An apparatus as set forth in claim 40 wherein said elongated force transmission component includes a cable connected with said metal spring.

42. An apparatus as set forth in claim 37 wherein said frame members are connected with a first limb of the human body, said framework further includes a second plurality of frame members which are connected with each other at a second plurality of frame joints, said elongated elastic force transmission component extends along said second plurality of frame members, said elongated force transmission component being resiliently extendable under the influence of force transmitted from the human body through said second frame members to said elongated force transmission component during movement of the human body.

43. An apparatus as set forth in claim 37 wherein said radius $r_1$ of said arcuate surface on said first pulley is larger than said radius $r_2$ of said arcuate surface on said second pulley and is smaller than said radius $r_3$ of said arcuate surface on said third pulley.

44. An apparatus as set forth in claim 37 wherein said elongate force transmission component engages portions of the arcuate surfaces on said first and second pulleys which are offset in a first direction from axes about which said first and second pulleys rotate, said elongated force transmission component engages a portion of the arcuate surface on said third pulley which is offset in a second direction from an axis about which said third pulley rotates.

45. An apparatus for use in assisting human body movement, said apparatus comprising a framework which includes a plurality of frame members which are connected with each other at a plurality of frame joints, said plurality of frame members being connectable with the human body with said frame joints adjacent to joints in the human body, an elastic force transmission system connected with said frame members to store energy during a first portion of the movement of the human body and for releasing the stored energy during a second portion of the movement of the human body, said elastic force transmission system includes an elongated force transmission component which extends along said framework, said elongated force transmission component being resiliently extendable under the influence of force transmitted through said framework to said elongated force transmission component during the first portion of the movement of the human body, said elongated force transmission component being resiliently contractible to transmit force from said elongated force transmission component to said framework during the second portion of the movement of the human body, said elongated force transmission component spans at least three joints in the human body, a first deflector disposed adjacent to a first frame joint which connects a first frame member with a second frame member, said first frame member being connectable with a pelvic portion of the human body and said second frame member being disposed adjacent to a femoral portion of the human body, said first and second frame members being interconnected by said first frame joint, said first frame joint and said first deflector being disposed adjacent to a hip joint in the human body when said first frame member is connected with the pelvic portion of the human body and said second frame member is disposed adjacent to the femoral portion of the human body, said first deflector being disposed in engagement with said elongated force transmission component at a location adjacent to the hip joint in the human body when said first frame member is connected with the pelvic portion of the human body and said second frame member is disposed adjacent to the femeral portion of the human body, a second deflector is disposed adjacent to a second frame joint which connects said second frame member with a third frame member, said third frame member being disposed adjacent to a tibial portion of the human body, said second frame joint and said second deflector being disposed adjacent to a knee joint in the human body when said second frame member is adjacent to the femoral portion of the human body and said third frame member is adjacent to the tibial portion of the human body, said second deflector being disposed in engagement with said elongated force transmission component at a location adjacent to the knee joint in the human body when said second frame member is disposed adjacent to the femoral portion of the human body and said third frame member is disposed adjacent to the tibial portion of the human body, and a third deflector is disposed adjacent to a third frame joint which connects said third frame member with a fourth frame member, said fourth frame member being connectable with a foot portion of the human body, said third frame joint and said third deflector being disposed adjacent to an ankle joint in the human body when said third frame member is adjacent to the tibial portion of the human body and said fourth frame member is connected with the foot portion of the human body, said third deflector being disposed in engagement with said elongated force transmission component at a location adjacent to the ankle joint in the human body when said third frame member is disposed adjacent to the tibial portion of the human body and said fourth frame member is connected with the foot portion of the human body.

46. An apparatus as set forth in claim 45 wherein each deflector of said plurality of deflectors includes a circular pulley which is rotatable under the influence of force transmitted to said pulley from said elongated force transmission component.

47. An apparatus as set forth in claim 45 wherein said elongated force transmission component includes a band which is formed of elastomeric material and is resiliently extended under the influence of force transmitted from said framework.

48. An apparatus as set forth in claim 45 wherein said elongated force transmission component includes a metal spring which is resiliently extended under the influence of force transmitted from said framework.

49. An apparatus as set forth in claim 48 wherein said elongated force transmission component includes a cable connected with said metal spring.

50. An apparatus as set fourth in claim 45 wherein said first deflector is a first pulley having an arcuate surface with a radius of $r_1$ and is rotatably disposed adjacent to said first frame joint, said second deflector is a second pulley having an arcuate surface with a radius of $r_2$ and is rotatably disposed adjacent to said second frame joint, and said third deflector is a third pulley having an arcuate surface with a radius of $r_3$, and is rotatably disposed adjacent to said third frame joint, said elastic force transmission system having a stiffness of k, said first and third arcuate surfaces being sized such that the product of $(r_1) \cdot (r_3) \cdot (k)$ is equal to between 51 and 95 Newton meters.

51. An apparatus as set forth in claim 50 wherein said radius $r_1$ of said arcuate surface on said first pulley is larger than said radius $r_2$ of said arcuate surface on said second pulley and is smaller than said radius $r_3$ of said arcuate surface on said third pulley.

52. An apparatus as set forth in claim 50 wherein said elongate force transmission component engages portions of the arcuate surfaces on said first and second pulleys which are offset in a first direction from axes about which said first and second pulleys rotate, said elongated force transmission component engages a portion of the arcuate surface on said third pulley which is offset in a second direction from an axis about which said third pulley rotates.

53. An apparatus as set forth in claim 45 further including a plurality of motors connected with said framework to provide force which assists in movement of the human body.

54. An apparatus an apparatus as set forth in claim 45 further including means for connecting said second frame member with the femoral portion of the human body and means for connecting said third frame member with the tibial portion of the human body.

55. An apparatus as set forth in claim 45 wherein said elongated force transmission component includes a band which is formed of elastomeric material and is resiliently extended under the influence of force transmitted from said framework.

56. An apparatus as set forth in claim 45 wherein said elongated force transmission component includes a metal spring which is resiliently extended under the influence of force transmitted from said framework.

57. An apparatus as set forth in claim 56 wherein said elongated force transmission component includes a cable connected with said metal spring.

58. An apparatus as set forth in claim 45 wherein said elastic force transmission system includes a plurality of pulleys which are rotatably mounted on said framework and are engaged by said elongated force transmission component.

59. An apparatus as set forth in claim 45 wherein said frame members are adapted to be connected with a first limb of the human body, said framework further includes a second plurality of frame members which are connected with each other at a second plurality of frame joints, said elongated elastic force transmission component extends along said second plurality of frame members, said elongated force transmission component being resiliently extendable under the influence of force transmitted from the human body through said second frame members to said elongated force transmission component during movement of the human body.

60. An apparatus as set fourth in claim 45 wherein said elastic force transmission system includes a first arcuate surface with a radius of $r_1$ and disposed adjacent to a first frame joint of said plurality of frame joints, a second arcuate surface with a radius of $r_2$ and disposed adjacent to a second frame joint of said plurality of frame joints, and a third arcuate surface with a radius of $r_3$, said first, second and third arcuate surfaces being connected with said framework, said elastic force transmission system having a stiffness of k, said first and third arcuate surfaces being sized such that the product of $(r_1) \cdot (r_3) \cdot (k)$ is equal to between 51 and 95 Newton meters, said elongated force transmission component being disposed in engagement with said first, second and third arcuate surfaces.

61. An apparatus as set forth in claim 60 wherein said radius $r_1$ of said first arcuate surface is larger than said radius $r_2$ of said second arcuate surface and is smaller than said radius $r_3$ of said third arcuate surface.

62. An apparatus as set forth in claim 60 wherein said elongated force transmission component engages a portion of said first arcuate surface which is on offset in a first direction from an axis through said first frame joint, said elongated force transmission component engages a portion of said second arcuate surface which is offset in the first direction from an axis through said second frame joint, said elongated force transmission component engages a portion of said third arcuate surface which is offset in a second direction from an axis through said third frame joint.

* * * * *